US012331030B2

(12) United States Patent
Zhang et al.

(10) Patent No.: US 12,331,030 B2
(45) Date of Patent: *Jun. 17, 2025

(54) PIPERIDINE-2,6-DIONE DERIVATIVES AND ULCERATIVE COLITIS TREATING

(71) Applicants: TIANJIN HEMAY PHARMACEUTICAL SCI-TECH CO., LTD, Tianjin (CN); GANZHOU HEMAY PHARMACEUTICAL, CO., LTD, Ganzhou (CN)

(72) Inventors: Hesheng Zhang, Tianjin (CN); Guanghuai Zeng, Tianjin (CN)

(73) Assignees: Tianjin Hemay Pharmaceutical Sci-Tech Co., Ltd, Tianjin (CN); Ganzhou Hemay Pharmaceutical, Co., Ltd, Ganzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/533,755

(22) Filed: Dec. 8, 2023

(65) Prior Publication Data

US 2024/0132466 A1 Apr. 25, 2024

Related U.S. Application Data

(60) Continuation of application No. 17/832,518, filed on Jun. 3, 2022, now Pat. No. 11,873,287, which is a division of application No. 16/464,224, filed as application No. PCT/CN2017/112668 on Nov. 23, 2017, now Pat. No. 11,485,724.

(30) Foreign Application Priority Data

Nov. 24, 2016 (CN) .......................... 201611041317.5

(51) Int. Cl.
| | | |
|---|---|---|
| C07D 401/04 | (2006.01) | |
| A61K 9/08 | (2006.01) | |
| A61P 1/00 | (2006.01) | |
| A61P 1/04 | (2006.01) | |
| A61K 9/20 | (2006.01) | |
| A61K 9/48 | (2006.01) | |

(52) U.S. Cl.
CPC .............. *C07D 401/04* (2013.01); *A61P 1/00* (2018.01); *A61P 1/04* (2018.01); *A61K 9/08* (2013.01); *A61K 9/2018* (2013.01); *A61K 9/4891* (2013.01)

(58) Field of Classification Search
CPC . C07D 401/14; A61P 1/00; A61P 1/04; A61K 9/08; A61K 9/2018; A61K 9/4891
See application file for complete search history.

(56) References Cited

U.S. PATENT DOCUMENTS

| | | | |
|---|---|---|---|
| 8,637,545 B2 | 1/2014 | Zhang | |
| 2008/0051432 A1* | 2/2008 | Zhang | ..................... A61P 35/00 |
| | | | 514/323 |
| 2016/0045484 A1 | 2/2016 | Tun | |
| 2019/0352277 A1 | 11/2019 | Zhang et al. | |

FOREIGN PATENT DOCUMENTS

| | | |
|---|---|---|
| CN | 1844118 A | 10/2006 |
| CN | 1961876 A | 5/2007 |
| WO | 02/070480 A1 | 9/2002 |
| WO | 2006/081251 A2 | 8/2006 |
| WO | 2006/105697 A1 | 10/2006 |
| WO | 2018/095378 A1 | 5/2018 |

OTHER PUBLICATIONS

Park & Jeen, Current and Emerging Biologics for Ulcerative Colitis, 9(1) Gut and Liver, 18-27 (2015) (Year: 2015).*
"Consensus on diagnosis and treatment of inflammatory bowel disease" *Chinese Journal of Gastroenterology* 17(12):763-781, 2012 (with English Abstract via Machine Translation).
Berlin et al., "Derivatives of 3-Aminopiperidine-2, 6-Dione," *Khimiya Geterotsiklicheskikh Soedinenii* 5(4): 652-654, 1969 (2 pages).
Braña et al., "Discovering a new analogue of thalidomide which may be used as a potent modulator of TNF-α production," *European Journal of Medicinal Chemistry* 44: 3533-3542, 2009.
Byun et al., "Synthesis and Hypnotic Activities of N-Cbz-α-aminoglutarimi-dooxy Carboxylate Derivatives," *Arch Pharm Res* 31(7):834-837, 2008.
Carter et al., "Clinically validated approaches to the treatment of autoimmune diseases," *Expert Opin. Investig. Drugs* 19(2): 195-213, 2010.
Cheng et al., "Nanotherapeutics in angiogenesis: synthesis and in vivo assessment of drug efficacy and biocompatibility in zebrafish embryos," *International Journal of Nanomedicine* 6:2007-2021 (2011).
He et al., "Clinical features of asthmatic-chronic obstructive pulmonary disease overlap syndrome," *Int. J. Respir.* 37(16):1207-1210, Aug. 2017. (w/ English Abstract).
He et al., "Preliminary study on serum IgE content in leprosy patients," *China Journal of Leprosy* 5(4):210-211, Dec. 1989. (w/ English Abstract) (3 pages).
Holgate, "New strategies with anti-IgE in allergic diseases," *World Allergy Organization Journal* 7:17, 2014. (7 pages).
International Search Report, mailed Jan. 26, 2018, for International Application No. PCT/CN2017/112668, 10 pages (w/ English translation).
International Search Report, mailed Mar. 13, 2018, for International Application No. PCT/CN2017/112669, 10 pages (w/ English translation).

(Continued)

*Primary Examiner* — Timothy R Rozof
(74) *Attorney, Agent, or Firm* — Seed IP Law Group LLP

(57) ABSTRACT

Disclosed are piperidine-2,6-dione derivatives and treatment of ulcerative colitis.

30 Claims, 2 Drawing Sheets

(56) References Cited

OTHER PUBLICATIONS

Kampmann et al., "The synthesis and fluorescence profile of novel thalidomide analogues," *Tetrahedron* 71(42): 8140-8149, 2015.
Kovács et al., "Synthesis of Glutamine and Pyroglutamylglutamine Derivatives Substituted in the Carboxamide Nitrogen," *Acta Physica et Chemica* 12(3-4): 143-150, 1966.
Lazzerini et al., "Effect of Thalidomide on Clinical Remission in Children and Adolescents With Refractory Crohn Disease, A Randomized Clinical Trial," *JAMA* 310(20):2164-2173, Nov. 27, 2013.
Li et al., "Estrogen aggravates inflammatory bowel disease in rats through estrogen receptor alpha," *Academic Journal of Second Military Medical University* 37(4):418-423, 2016 (with English abstract).
Li et al., "Expression and Significance of IGE in Nasal Mucosa of Patients with Allergic Rhinitis," *J. Prev. Med. Chin. PLA* 36(10):1238-1240, Oct. 2018. (w/ English Abstract).
Padwa et al., "Diels-Alder Reaction of 2-Amino-Substituted Furans as a Method for Preparing Substituted Anilines," *J. Org. Chem.* 62(12):4088-4096, 1997.
Plamondon et al., "Thalidomide in luminal and fistulizing Crohn's disease resistant to standrad therapies," *Aliment. Pharmacol. Ther.* 25:557-567, 2007.
RN 710935-25-4, Registry, enter STN: Jul. 16, 2004.
RN 937844-56-9, Registry, enter STN: Jun. 19, 2007.
RN 937844-57-0, Registry, enter STN: Jun. 19, 2007.
RN 937844-58-1, Registry, enter STN: Jun. 19, 2007.
Rogler, "Editorial: is thalidomide a good option for patients with refractory Crohn's disease?," *Aliment. Pharmacol. Ther.* 41:785-788, 2015.
Scribano et al., "Mucosal Healing With Thalidomide in Refractory Crohn's Disease Patients Intolerant of Anti-TNF-α Drugs," *J. Clin. Gastroenterol.* 48:530-533, 2014.
Videla et al., "Selective Inhibition of Phosphodiesterase-4 Ameliorates Chronic Colitis and Prevents Intestinal Fibrosis," *The Journal of Pharmacology and Experimental Therapeutics* 316(2): 940-945, 2006.
Wang et al., "Establishment of Inflammatory Bowel Disease Models induced by 2, 4, 6-Trinitrobenzenesulfonic Acid in Rats," *J. Med. Res.* 37(7):42-44, Jul. 2008. (w/ English Abstract) (4 pages).
Wang et al., "Research progress in the treatment of IgE related allergic diseases," *Clin. J. Med. Offic.* 45(8):872-874, Aug. 2017. (w/ English Abstract) (4 pages).
Xu et al., "Detection of total IgE and specific IgE in patients with chronic measles," *Acta Universiatis Medicinalis Secondae Shanghai* 14(Suppl. 1994):118-120, 1994. (w/ English Abstract) (4 pages).
Yang et al., "Systematic review: thalidomide and thalidomide analogues for treatment of inflammatory bowel disease," *Alimentary Pharmacology and Therapeutics* 41: 1079-1093, 2015.
Yin et al., "Current status of drug therapy for acute cerebral infarction," *Chinese Pharmaceutical Meeting and Chinese Pharmacist Week*, Abstract Only, 2010. (w/ English Abstract) (9 pages).
Yin et al., "Research progress on the relationship between IgE and autoimmune diseases," *Chin. J. Lab. Med.* 41(3):242-245, Mar. 2018. (w/ English Abstract).
Zhang et al., "Detection of serum IgE and analysis of allergens in children with specific dermatitis and chronic urticaria," *Guangdong Medical Journal* 28(10):1688-1690, Oct. 2007. (w/ English Abstract) (4 pages).
Zhang et al., "Roles of Glutathione in dextran sodium sulphate-induced colitis in mice," *World Chin J Digestol* 13(12):1400-1403, 2005 (with English abstract).
Zhao et al., "Role of IgE in allergic asthma and anti-IgE therapy," *Journal of Clinical Pulmonary Medicine* 23(7):1325-1328, Jul. 2018. (w/ English Abstract) (5 pages).

\* cited by examiner

PIPERIDINE-2,6-DIONE DERIVATIVES AND ULCERATIVE COLITIS TREATING

RELATED APPLICATION

The present disclosure claims all the benefits of the patent application No. 201611041317.5 which was filed on Nov. 24, 2016 before the State Intellectual Property Office of the People's Republic of China and was entitled "Use of Piperidine-2,6-dione Derivatives for Treating Ulcerative Colitis", which is incorporated herein by reference in its entirety.

FIELD

The present disclosure relates to organic chemistry and medicinal chemistry fields.

BACKGROUND

Ulcerative colitis (UC) is a non-specific inflammatory disease, of which the pathogeny is not yet clear. Most cases start from the terminal ileum. Under the microscope, ulcerative colitis is limited to the mucosa (intestinal epithelium). Ulcerative colitis lesion is limited to the colorectal mucosa and submucosa. The pathological changes mostly occur in the sigmoid colon and rectum, and also extend to descending colon, and even in the entire colon. The course of disease is lengthy. The disease often repeatedly attacks. The less common ulcerative colitis can be concurrent with severe bloody diarrhea and toxic megacolon, which requires surgical treatment. Ulcerative colitis is associated with the increased risk of gastrointestinal malignant cancer. Ulcerative colitis has a different proportion of parenteral manifestations (such as liver problems, arthritis, skin manifestations and eye problems). It is found by researches that ulcerative colitis is associated with TH2 (type 2 helper cells) mediated humoral immunity.

The clinical manifestations of ulcerative colitis include continuous or recurrent diarrhea, mucopurulent bloody stool accompanied by abdominal pain, tenesmus and various degrees of systemic symptoms. The course is generally more than 4-6 weeks. The extraintestinal manifestations such as skin, mucous membranes, joints, eyes, hepatobiliary and the like may be occurred. Colonoscopy and biopsy are the main basis for the diagnosis of ulcerative colitis. Under colonoscopy, ulcerative colitis lesion occurs from the rectum, which is continuous and diffuse distribution. The manifestations include that (I) textures of mucosal blood vessels become blurred, disorder or disappeared, hyperaemia, edema, friable, spontaneous or contact bleeding, and purulent secretion attachment, and mucosa becoming rough and granular; (2) diffuse and multiple erosion or ulcers can be obviously seen at lesion sites; and (3) it can be seen that colon bag becomes shallow, blunt or disappeared as well as fake polyps, mucosal bridge and so on. The following major histological changes can been seen: Active period: (1) intrinsic membrane diffuse, acute, chronic inflammatory cell infiltration, including neutrophils, lymphocytes, plasma cells, eosinophils and so on, especially neutrophil infiltration in epithelial cells and cryptitis, and even the formation of crypt abscess; (2) structural changes of crypt, irregular crypt sizes and shapes, arrangement of crypt in disorder, and goblet cells becoming decreased; and (3) visible mucosal surface erosion, shallow ulcer formation and granulation tissue hyperplasia. Remission period: (1) mucosal erosion or ulcer becomes healed; (2) intrinsic membrane neutrophil infiltration becomes decreased or disappeared, chronic inflammatory cells become decreased; and (3) structural changes of crypt can be aggravated, such as crypt reduction, atrophy, and visible Paneth cell metaplasia.

The main drugs for the treatment of active ulcerative colitis comprise 5-aminosalicylic acid (5-ASA) (such as sulfasalazine and mesalazine), glucocorticoids, mercaptopurines, immunosuppressants (such as ciclosporin A) and monoclonal antibodies (TNF-α monoclonal antibodies). The mild to moderate ulcerative colitis is treated with aminosalicylic acid drugs alone or combined with mercaptopurine drugs. If the above treatment is ineffective, the use of systemic hormonal drugs can be considered. If aminosalicylic acids, mercaptopurines and systemic hormonal drugs are ineffective to treat patients having moderate and severe ulcerative colitis, it is recommended to use TNF-α monoclonal antibodies. The treatment of ulcerative colitis in remission mainly focuses the maintenance treatment, in which the drugs generally comprise aminosalicylic acids, mercaptopurines and TNF-α monoclonal antibodies.

It is found during the use of 5-aminosalicylic acid drugs that about 50% of patients suffer vomiting, anepithymia, liver dysfunction and other digestive disorders, hemolytic anemia and folic acid deficiency anemia and other blood disorders. In addition, since there is a salicylic acid skeleton, there is a possibility that side effects such as diarrhea, abdominal pain, amylase rise, and renal dysfunction occur in cases where the patients have allergic symptoms on salicylic acid agents. Furthermore, because it is discovered that sulfasalazine has side effects of male infertility and colored urine, the patients suffer great mental stress. Due to immunosuppression and short-term efficacy characteristics, corticosteroids such as prednisone or budesonide can also be used. Among corticosteroids, beclomethasone dipropionate may be effective in long-term treatment of post-acute patients, Corticosteroid formulations have side effects such as osteoporosis, growth disorders, secondary adrenal insufficiency, abnormal sugar tolerance, high blood pressure and the like. Given that the risk is greater than the benefit, corticosteroid formulations are not used for long-term treatment. Where the patients cannot be relieved with 5-ASA and corticosteroids, immunosuppressive drugs such as azathioprine, and biological agents such as infliximab and adalimumab are finally administered. Monoclonal antibody drugs may cause high blood pressure, chills, rash, fever, headache, eczema and so on. As intliximab is a chimeric antibody, it is possible to show antigenicity and sometimes cause acute hypersensitivity. Moreover, when the patients are not administered with the biological agents, it will lead to the recurrence of the disease and increase difficulty to treat the disease. The biological agents will also give patients a greater financial burden.

Ulcerative colitis is a chronic disease that requires a lengthy duration of drugs. The above data show that there is no drug for long-term effective treatment of ulcerative colitis, especially drug by oral administration. Therefore, there is a need for developing better target therapy with optimized chronic use for ulcerative colitis, or drugs with better effectiveness or better safety.

SUMMARY

Glucose sodium sulfate (DSS)-induced inflammatory bowel disease model is widely used to study the mechanism of ulcerative colitis and the development and assessment of drugs for treating ulcerative colitis. See the following references: LI Wen-xin, JIANG Qian, MA Bei, "Estrogen aggravates inflammatory bowel disease in rats through estrogen receptor alpha"; Academic Journal of Second Military Medical University: 2016, 37(4). ZHANG ling et al., "Roles of Glutathione in dextran sodium sulphate-induced colitis in mice"; World Chinese Journal of Digestology, 2005 Jun. 28:13(12):1400-1403, which are incorporated herein by reference in its entirety.

In one aspect, some embodiments disclose a piperidine-2,6-dione derivative of formula (I) and pharmaceutically acceptable salts thereof:

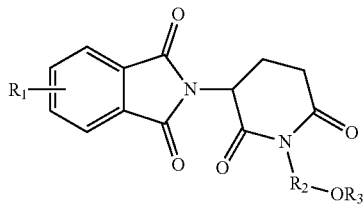

formula (I)

wherein, $R_1$ represents one or more substituents selected from the group consisting of H, halogen, —OH, —$C_{1-4}$alkyl, —$NH_2$, —$NHC_{1-4}$alkyl, —$N(C_{1-4}$alkyl$)_2$ and —$NHCOC_{1-4}$alkyl;

$R_2$ represents —$CH_2CH_2$—, —$CH_2CH_2CH_2$— or —$CH_2CH_2CH_2CH_2$—; and $R_3$ represents —H or —$C_{1-4}$alkyl.

In another aspect, some embodiments disclose a piperidine-2,6-dione derivative of formula (II) and pharmaceutically acceptable salts thereof:

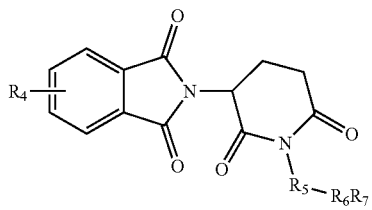

formula (II)

wherein, $R_4$ represents one or more substituents selected from the group consisting of H, halogen, —$C_{1-4}$alkyl, —$NH_2$, —$NHC_{1-4}$alkyl, —$N(C_{1-4}$alkyl$)_2$ and —$NHCOC_{1-4}$alkyl;

$R_5$ represents —$CH_2CH_2$—, —$CH_2CH_2CH_2$— or —$CH_2CH_2CH_2CH_2$—;

$R_6$ represents —S—, —SO—, —$SO_2$—, —NH— or —$N(C_{1-4}$alkyl)-; and $R_7$ represents —H or —$C_{1-4}$alkyl.

In yet another aspect, some embodiments disclose a piperidine-2,6-dione derivative of formula (III) and pharmaceutically acceptable salts thereof:

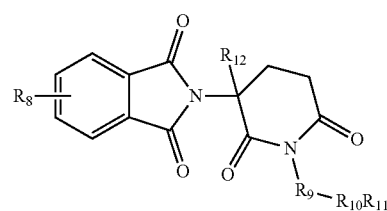

formula (III)

wherein, $R_8$ represents one or more substituents selected from the group consisting of H, halogen, —$C_{1-4}$alkyl, —$NH_2$, —$NHC_{1-4}$alkyl, —$N(C_{1-4}$alkyl$)_2$ and —$NHCOC_{1-4}$alkyl;

$R_9$ represents —$CH_2CH_2$—, —$CH_2CH_2CH_2$— or —$CH_2CH_2CH_2CH_2$—;

$R_{10}$ represents —O—, —S—, —SO—, —$SO_2$—, —NH— or —$N(C_{1-4}$alkyl)-;

$R_{11}$ represents —H or —$C_{1-4}$alkyl; and $R_{12}$ represents halogen or —$C_{1-4}$alkyl.

All the compounds of formula (I), formula (II) and formula (III) as mentioned above belong to piperidine-2,6-dione derivatives as mentioned herein.

In still another aspect, some embodiments disclose a piperidine-2,6-dione derivative and pharmaceutically acceptable salts thereof, which are selected from the group consisting of:

4-acetylamino-2-(1-(2-methoxyethyl)-2,6-dioxopiperidin-3-yl)isoindolin-1,3-dione and pharmaceutically acceptable salts thereof;

4-methylamino-2-(1-(2-methoxyethyl)-2,6-dioxopiperidin-3-yl)isoindolin-1,3-dione and pharmaceutically acceptable salts thereof;

4-dimethylamino-2-(1-(2-methoxyethyl)-2,6-dioxopiperidin-3-yl)isoindolin-1,3-dione and pharmaceutically acceptable salts thereof;

4-fluoro-2-(1-(2-methoxyethyl)-2,6-dioxopiperidin-3-yl)isoindolin-1,3-dione and pharmaceutically acceptable salts thereof;

4,5,6,7-tetrafluoro-2-(1-(2-methoxyethyl)-2,6-dioxopiperidin-3-yl)isoindolin-1,3-dione and pharmaceutically acceptable salts thereof;

4-amino-2-(1-(2-hydroxyethyl)-2,6-dioxopiperidin-3-yl)isoindolin-1,3-dione and pharmaceutically acceptable salts thereof;

5-amino-2-(1-(2-methoxyethyl)-2,6-dioxopiperidin-3-yl)isoindolin-1,3-dione and pharmaceutically acceptable salts thereof;

4-amino-5-hydroxy-2-(1-(2-methoxyethyl)-2,6-dioxopiperidin-3-yl)isoindolin-1,3-dione and pharmaceutically acceptable salts thereof;

4-amino-5-fluoro-2-(1-(2-methoxyethyl)-2,6-dioxopiperidin-3-yl)isoindolin-1,3-dione and pharmaceutically acceptable salts thereof;

4-amino-7-hydroxy-2-(1-(2-methoxyethyl)-2,6-dioxopiperidin-3-yl)isoindolin-1,3-dione and pharmaceutically acceptable salts thereof;

4-amino-2-(1-(2-methylthioethyl)-2,6-dioxopiperidin-3-yl)isoindolin-1,3-dione and pharmaceutically acceptable salts thereof;

4-amino-2-(1-(2-methylsulfinylethyl)-2,6-dioxopiperidin-3-yl)isoindolin-1,3-dione and pharmaceutically acceptable salts thereof;

4-amino-2-(1-(2-methylsulfonylethyl)-2,6-dioxopiperidin-3-yl)isoindolin-1,3-dione and pharmaceutically acceptable salts thereof;

4-amino-2-(1-(2-methoxyethyl)-3-fluoro-2,6-dioxopiperidin-3-yl)isoindolin-1,3-dione and pharmaceutically acceptable salts thereof;

4-amino-2-(1-(2-methoxyethyl)-3-methyl-2,6-dioxopiperidin-3-yl)isoindolin-1,3-dione and pharmaceutically acceptable salts thereof;

4-acetylamino-2-(1-(2-methoxypropyl)-2,6-dioxopiperidin-3-yl)isoindolin-1,3-dione and pharmaceutically acceptable salts thereof;

4-fluoro-2-(1-(2-methoxypropyl)-2,6-dioxopiperidin-3-yl)isoindolin-1,3-dione and pharmaceutically acceptable salts thereof;

5-amino-2-(1-(2-methoxypropyl)-2,6-dioxopiperidin-3-yl)isoindolin-1,3-dione and pharmaceutically acceptable salts thereof;

4-amino-2-(1-(2-ethoxyethyl)-2,6-dioxopiperidin-3-yl)isoindolin-1,3-dione and pharmaceutically acceptable salts thereof;

4-fluoro-2-(1-(2-ethoxyethyl)-2,6-dioxopiperidin-3-yl)isoindolin-1,3-dione and pharmaceutically acceptable salts thereof;

5-fluoro-2-(1-(2-methoxyethyl)-2,6-dioxopiperidin-3-yl)-isoindolin-1,3-dione and pharmaceutically acceptable salts thereof;

4-amino-2-(1-(2-methoxybutyl)-2,6-dioxopiperidin-3-yl)isoindolin-1,3-dione and pharmaceutically acceptable salts thereof;

4-hydroxy-2-(1-(2-methoxyethyl)-2,6-dioxopiperidin-3-yl)isoindolin-1,3-dione and pharmaceutically acceptable salts thereof;

4-methyl-2-(1-(2-methoxyethyl)-2,6-dioxopiperidin-3-yl)-isoindolin-1,3-dione and pharmaceutically acceptable salts thereof;

4-amino-5-methoxy-2-(1-(2-methoxyethyl)-2,6-dioxopiperidin-3-yl)-isoindolin-1,3-dione and pharmaceutically acceptable salts thereof;

4-amino-2-(1-(2-methoxyethyl)-2,6-dioxopiperidin-3-yl)isoindolin-1,3-dione and pharmaceutically acceptable salts thereof; and 4-amino-2-(1-(2-methoxypropyl)-2,6-dioxopiperidin-3-yl)isoindolin-1,3-dione and pharmaceutically acceptable salts thereof.

In another aspect, some embodiments disclose a pharmaceutical composition comprising the piperidine-2,6-dione derivative or pharmaceutically acceptable salts thereof as disclosed herein, and a pharmaceutically acceptable carrier, diluent or excipient.

In another aspect, some embodiments disclose a method for treating ulcerative colitis, comprising administering a therapeutically effective amount of the piperidine-2,6-dione derivative or pharmaceutically acceptable salts thereof as disclosed herein, or a therapeutically effective amount of the pharmaceutical composition as disclosed herein to a subject in need thereof.

In another aspect, some embodiments disclose the piperidine-2,6-dione derivative and pharmaceutically acceptable salts thereof of as disclosed herein for treating ulcerative colitis.

In another aspect, some embodiments disclose a pharmaceutical composition for treating ulcerative colitis, comprising the piperidine-2,6-dione derivative or pharmaceutically acceptable salts thereof as disclosed herein, and a pharmaceutically acceptable carrier, diluent or excipient.

DETAILED DESCRIPTION

Figure 1:
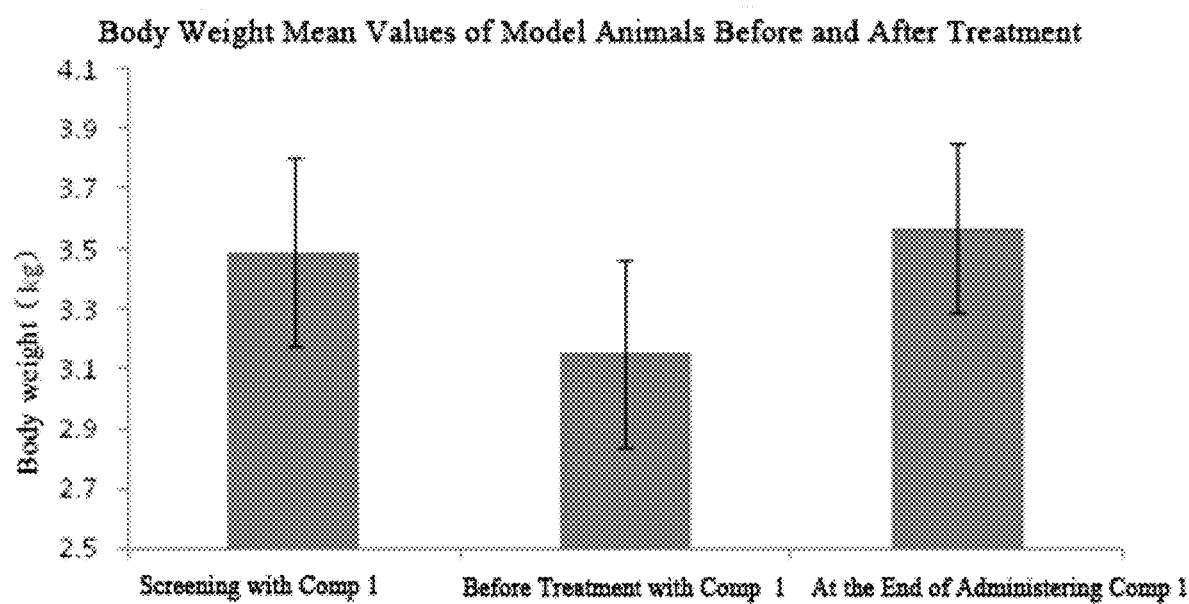
FIG. 1 shows the weight mean values of animals before and after treatment.
Figure 2:
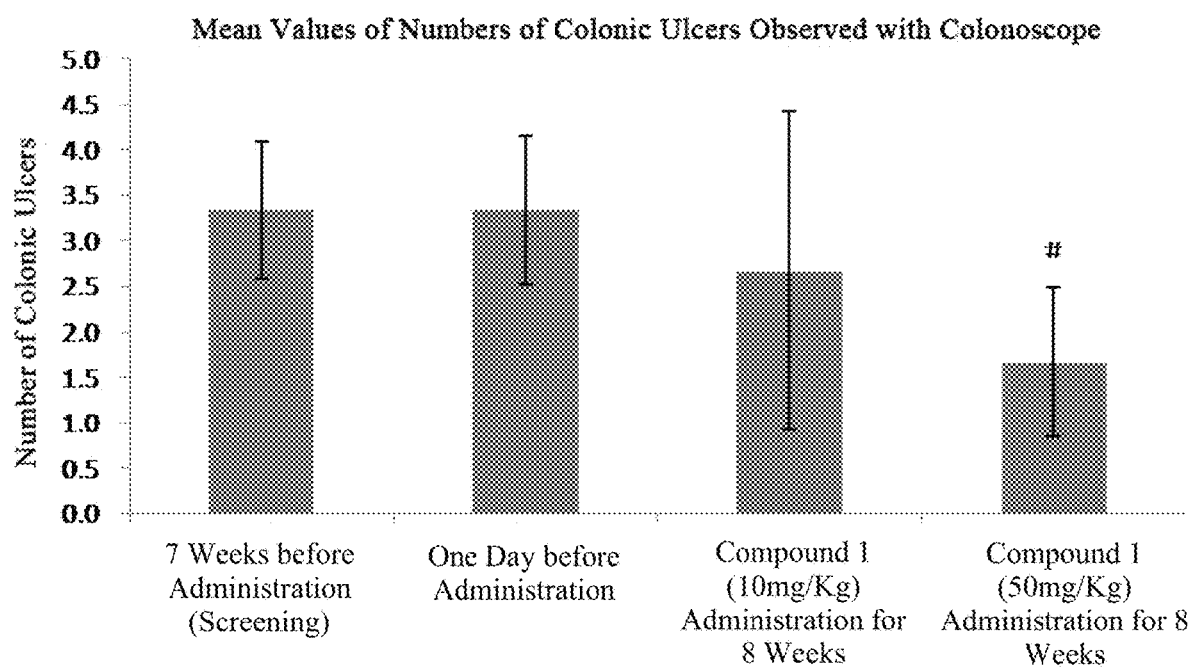
FIG. 2 shows the mean values of colonic ulcers observed with colonoscope.

In the following description, certain specific details are included to provide a thorough understanding for various disclosed embodiments. One skilled in the relevant art, however, will recognize that the embodiments may be practiced without one or more these specific details, or with other methods, components, materials, etc.

Unless the context required otherwise, throughout the specification and claims which follows, the term "comprise" and variations thereof, such as "comprises" and "comprising" are to be construed in an open, inclusive sense, which is as "include, but not limited to".

Reference throughout this specification to "one embodiment", or "an embodiment", or "in another embodiment", or "in some embodiments" means that a particular referent feature, structure or characteristic described in connection with the embodiments is included in at least one embodiment. Therefore, the appearance of the phrases "in one embodiment", or "in the embodiment", or "in another embodiment", or "in some embodiments" in various places throughout this specification are not necessarily all referring to the same embodiment. Moreover, the particular features, structures or characteristics may be combined in any suitable manner in one or more embodiments.

Definition

Accordingly, as used in the specification and appended claims, unless specified to the contrary, the following terms have the meanings indicated:

The term "ulcerative colitis" is a nonspecific inflammatory disease, of which the etiology is not yet clear. The initial manifestations of ulcerative colitis may have many forms. Bloody diarrhea is the most common early symptom. Other symptoms successively comprises abdominal pain, blood loss, weight loss, tenesmus, vomiting, and the like. Occasional symptoms comprise arthritis, iridocyclitis, liver dysfunction and skin lesions, Fever is a relatively unusual symptom. Among most patients, the manifestation of the disease is chronic and low-malignant. The course of disease is acute and catastrophic in a small number of patients (about 15%), whose manifestations comprise, up to 30 times per day of frequent bloody feces, high fever and abdominal pain. The more specific definition can be found in the following reference: Consensus on diagnosis and treatment of inflammatory bowel disease (2012, Guangzhou), Chinese Journal of Gastroenterology, 2012, 51 (12):763-781, which is incorporated herein by reference in its entirety.

Ulcerative colitis can be mild ulcerative colitis, moderate ulcerative colitis, severe ulcerative colitis or ulcerative colitis in remission.

The above classification of ulcerative colitis is defined according to the following method:

TABLE 1

Modified Mayo Scoring System for Assessment of Ulcerative Colitis

| Items | 0 point | 1 point | 2 points | 3 points |
|---|---|---|---|---|
| Stool Frequency[a] | Normal number of stools for patient | 1 to 2 stools per day more than normal | 3 to 4 stools per day more than normal | >=5 stools per day more than normal |
| Bloody Stool[b] | No blood seen | Streaks of blood with stool less than half the time | Obvious blood with stool most of the time. | Blood alone passes |
| Endoscopic findings | Normal or inactive disease | Mild disease (erythema, decreased vascular pattern, mild friability) | Moderate disease (marked erythema, lack of vascular pattern, friability, erosions) | Severe disease (spontaneous bleeding, ulceration) |
| Physician's Global Assessment[c] | Normal | Mild disease | Moderate disease | Severe disease |

[a]Each patient serves as his or her own control to establish the degree of abnormality of the stool frequency.
[b]The daily bleeding score represents the most severe bleeding of the day.
[c]The physician's global assessment acknowledges the three other criteria, the patient's daily recollection of abdominal discomfort and general sense of well being, and other observations, such as physical findings and patient's performance status.

Clinical remission: Mayo Score of less than or equal to 2 with no individual subscore greater than 1. Mild: Mayo Score of 3 to 5. Moderate: Mayo Score of 6 to 10. Severe: Mayo Score of 11 to 12. Clinical response: Reduction in Mayo score of greater than or equal to 3 points and greater than or equal to 30 percent from baseline with an accompanying decrease in bloody stool subscore of greater than or equal to 1 point or absolute bloody stool subscore of less than or equal to 1 point.

The patient's conditions are scored according to the modified Mayo scoring system. The clinical remission after assessment corresponds to the ulcerative colitis in remission of the present disclosure. The mild activity corresponds to the mild ulcerative colitis of the present disclosure. The moderate activity corresponds to moderate ulcerative colitis of the present disclosure. The severe activity corresponds to the severe ulcerative colitis of the present disclosure.

Certain chemical groups named herein are preceded by a shorthand notation indicating the total number of carbon atoms that are to be found in the indicated chemical group. For example, $C_1$-$C_4$ alkyl describes an alkyl group, as defined below, having a total of 1 to 4 carbon atoms, and $C_3$-$C_{10}$cycloalkyl describes a cycloaklyl group, as defined below, having a total of 3 to 10 carbon atoms. The total number of carbon atoms in the shorthand notation does not include the carbons that may exist in the substituents of the groups described.

The term "halogen" refers to fluoro, chloro, bromo or iodo.

The term "alkyl" refers to a straight or branched hydrocarbon chain group consisting solely of carbon and hydrogen, containing no unsaturation, having from one to twelve carbon atoms and which is attached to the rest of the molecule by a single bond. In some embodiments, alkyl has one to eight carbon atoms. In some embodiments, alkyl has one to six carbon atoms. In some embodiments, alkyl has one to four carbon atoms. Exemplary examples of alkyls include but are not limited to methyl, ethyl, n-propyl, 1-methylethyl (iso-propyl), n-butyl, n-pentyl, 1,1-dimethylethyl (tert-butyl), 3-methylhexyl, 2-methylhexyl, and the like.

The term "mammal" means animals including, for example, dogs, cats, cows, sheep, horses, and humans. In some embodiments, mammals include humans.

The term "patient" means an animal, such as a human, a companion animal, such as a dog, cat and horse, and livestock, such as cattle, swine and sheep. In some embodiments, patients are mammals, including both males and females. In some embodiments, patients are humans.

The term "pharmaceutically acceptable" as used herein means the carrier, vehicle, diluent, excipient and/or salt must be compatible with the other ingredients of the formulation, and not deleterious to the recipient thereof.

"Optional" or "optionally" means that the subsequently described event of circumstances may or may not occur, and that the description includes instances where said event or circumstance occurs and instances in which it does not.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isosmotic agent, solvent, or emulsifier, etc, which has been approved by the United States Food and Drug Administration as being acceptable for use in humans or animals and have no side effects on preparing a pharmaceutical composition.

"Pharmaceutically acceptable salts" include both "pharmaceutically acceptable acid addition salts" and "pharmaceutically acceptable base addition salts".

"Pharmaceutically acceptable acid addition salt" refers to those salts which retain the biological effectiveness and properties of the free bases, which are not biologically or otherwise undesirable, and which are formed with inorganic acids such as, but not limited to hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphanic acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleinic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid and the like.

"Pharmaceutically acceptable base addition salt" refers to those salts which retain the biological effectiveness and properties of the free acids, which are not biologically or otherwise undesirable. These salts are prepared from addition of an inorganic or an organic base to the free acid. Salts derived from inorganic bases include, but are not limited to, sodium, potassium, lithium, ammonium, calcium, magnesium, iron, zinc, copper, manganese, aluminium salts and the like. In some embodiments, inorganic salts are the ammonium, sodium, potassium, calcium, and magnesium salts. Salts derived from organic bases include, but are not limited to, salts of primary, secondary and tertiary amines, substituted amines including naturally occurring substituted amines, cyclic amines and s basic ion exchange resins, such as ammonia, isopropylamine, trimethylamine, diethylamine, triethylamine, tripropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucosamine, theobromine, triethanolamine, trometamol, purine, piperazine, piperidine, N-ethyl piperidine, polyamine resins and the like. In some embodiments, organic bases are isopropylamine, diethylamine, ethanolamine, trimethylamine, dicyclohexylamine, choline and caffeine.

The term "a solvent or a solvent mixture" refers to any and all solvents. In some embodiments, a solvent or a solvent mixture is organic solvents and water, which include, but are not limited to, water, methanol, ethanol, 2-propanol, n-butanol, iso-butanol, acetone, methylethylketone, ethylacetate, 1,4-dioxane, diethylether, MTBE, THF, acetonitrile, dichloromethane, chloroform, DMF, cyclohexane, cyclopentane, n-hexane, n-heptane, n-pentane, toluene, o-xylene, p-xylene, DMSO, pyridine, acetic acid, anisole, butylacetate, cumene, ethylformate, formic acid, isobutylacetate, iso-propylacetate, methylacetate, 3-methyl-1-butanol, methylisobutylketone, 2-methyl-1-propanol, 1-pentanol, propylacetate, ethylenglycole, and 1-methyl-2-pyrrolidone, as well as any and all mixtures of two or more such solvents. In some embodiments, a solvent or a solvent mixture is single solvent and binary mixtures. In some embodiments, a solvent or a solvent mixture is water and single solvent of organic solvent and binary mixtures of water and organic solvent.

A "pharmaceutical composition" refers to a formulation of a compound of the present disclosure and a medium generally acceptable in the art for the delivery of the biologically active compound to mammals, e.g., humans. Such a medium includes all pharmaceutically acceptable carriers, diluents or excipients therefor.

"Therapeutically effective amount" refers to an amount of a compound or combination of compounds that ameliorates, attenuates or eliminates a particular disease or condition or a symptom of a particular disease or condition, or prevents or delays the onset of a particular disease or condition or a symptom of a particular disease or condition. The amount of a compound of the present disclosure which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, such as a human, having the disease or disorder of interest, and includes:
(i) preventing the disease or condition from occurring in a mammal, in particular, when such mammal is predisposed to the condition but has not yet been diagnosed as having it;
(ii) inhibiting the disease or condition, i.e., arresting its development; or
(iii) relieving the disease or condition, i.e., causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the present disclosure or their pharmaceutically acceptable salt may contain one or more asymmetric centers and may thus give rise to enantiomers, diastereoisomers, and other stereoismeric forms that may be defined, in terms of absolute stereochemistry, as (R)- or (S)-, or (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof.

The substituent position of the compounds disclosed in the present disclosure is numbered as follows:

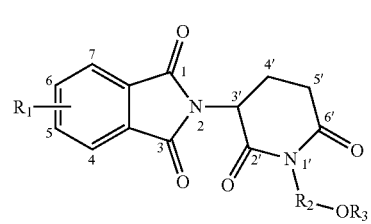

formula (I)

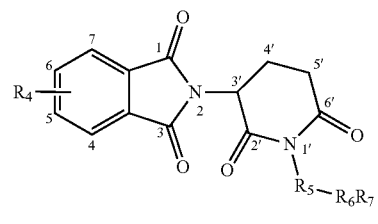

formular (II)

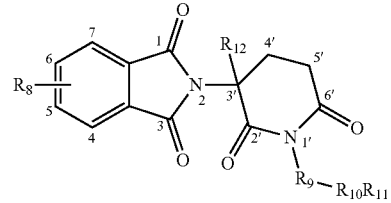

formula (III)

The substitution site of $R_1$ in formula (I) can be one of the sites numbered as 4, 5, 6 and 7 or a combination of several sites numbered as 4, 5, 6 and 7. The substitution site of $R_4$ in formula (II) can be one of the sites numbered as 4, 5, 6 and 7 or a combination of several sites numbered as 4, 5, 6 and 7. The substitution site of $R_8$ in formula (III) can be one of the sites numbered as 4, 5, 6 and 7 or a combination of several sites numbered as 4, 5, 6 and 7.

Specific Embodiments

In one aspect, some embodiments disclose a piperidine-2,6-dione derivative of formula (I) and pharmaceutically acceptable salts thereof:

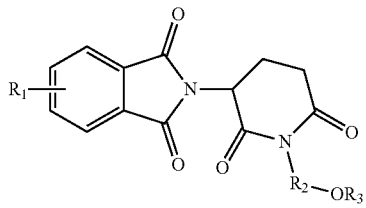

formula (I)

wherein,
$R_1$ represents one or more substituents selected from the group consisting of H, halogen, —OH, —$C_{1-4}$alkyl, —$NH_2$, —$NHC_{1-4}$alkyl, —$N(C_{1-4}alkyl)_2$ and —$NHCOC_{1-4}$alkyl;
$R_2$ represents —$CH_2CH_2$—, —$CH_2CH_2CH_2$— or —$CH_2CH_2CH_2CH_2$—; and
$R_3$ represents —H or —$C_{1-4}$alkyl.

Some embodiments disclose a piperidine-2,6-dione derivative of formula (I) and pharmaceutically acceptable salts thereof:

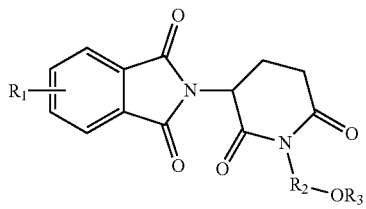

formula (I)

wherein,
$R_1$ represents one or more substituents selected from the group consisting of —H, —F, —Cl, —Br, —OH, —$CH_3$, —$CH_2CH_3$, —$CH_2CH_2CH_3$, —$NHCH_3$, —$NH_2$, —$NHCH_2CH_3$, —$N(CH_3)_2$, —$N(CH_2CH_3)_2$, —$NHCOCH_3$ and —$NHCOCH_2CH_3$;
$R_2$ represents —$CH_2CH_2$—, —$CH_2CH_2CH_2$— or —$CH_2CH_2CH_2CH_2$—; and
$R_3$ represents —H, —$CH_3$ or —$CH_2CH_3$.

Some embodiments disclose a piperidine-2,6-dione derivative of formula (I) and pharmaceutically acceptable salts thereof:

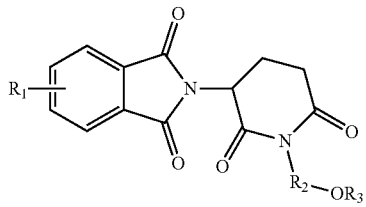

formula (I)

wherein,
$R_1$ represents one or more substituents selected from the group consisting of —H, —F, —OH, —$CH_3$, —$NHCH_3$, —$N(CH_3)_2$, —$NHCOCH_3$ and —$NH_2$;
$R_2$ represents —$CH_2CH_2$—, —$CH_2CH_2CH_2$— or —$CH_2CH_2CH_2CH_2$—; and
$R_3$ represents —H, —$CH_3$ or —$CH_2CH_3$.

Some embodiments disclose a piperidine-2,6-dione derivatives of formula (I) and pharmaceutically acceptable salts thereof, which are selected from the group consisting of:

4-acetylamino-2-(1-(2-methoxyethyl)-2,6-dioxopiperidin-3-yl)isoindolin-1,3-dione and pharmaceutically acceptable salts thereof;

4-methylamino-2-(1-(2-methoxyethyl)-2,6-dioxopiperidin-3-yl)isoindolin-1,3-dione and pharmaceutically acceptable salts thereof;

4-dimethylamino-2-(1-(2-methoxyethyl)-2,6-dioxopiperidin-3-yl)isoindolin-1,3-dione and pharmaceutically acceptable salts thereof;

4-fluoro-2-(1-(2-methoxyethyl)-2,6-dioxopiperidin-3-yl)isoindolin-1,3-dione and pharmaceutically acceptable salts thereof;

4,5,6,7-tetrafluoro-2-(1-(2-methoxyethyl)-2,6-dioxopiperidin-3-yl)isoindolin-1,3-dione and pharmaceutically acceptable salts thereof;

4-amino-2-(1-(2-hydroxyethyl)-2,6-dioxopiperidin-3-yl)isoindolin-1,3-dione and pharmaceutically acceptable salts thereof;

5-amino-2-(1-(2-methoxyethyl)-2,6-dioxopiperidin-3-yl)isoindolin-1,3-dione and pharmaceutically acceptable salts thereof;

4-amino-5-hydroxy-2-(1-(2-methoxyethyl)-2,6-dioxopiperidin-3-yl)isoindolin-1,3-dione and pharmaceutically acceptable salts thereof;

4-amino-5-fluoro-2-(1-(2-methoxyethyl)-2,6-dioxopiperidin-3-yl)isoindolin-1,3-dione and pharmaceutically acceptable salts thereof;

4-amino-7-hydroxy-2-(1-(2-methoxyethyl)-2,6-dioxopiperidin-3-yl)isoindolin-1,3-dione and pharmaceutically acceptable salts thereof;

4-acetylamino-2-(1-(2-methoxypropyl)-2,6-dioxopiperidin-3-yl)isoindolin-1,3-dione and pharmaceutically acceptable salts thereof;

4-fluoro-2-(1-(2-methoxypropyl)-2,6-dioxopiperidin-3-yl)isoindolin-1,3-dione and pharmaceutically acceptable salts thereof;

5-amino-2-(1-(2-methoxypropyl)-2,6-dioxopiperidin-3-yl)isoindolin-1,3-dione and pharmaceutically acceptable salts thereof;

4-amino-2-(1-(2-ethoxyethyl)-2,6-dioxopiperidin-3-yl)isoindolin-1,3-dione and pharmaceutically acceptable salts thereof;

4-fluoro-2-(1-(2-ethoxyethyl)-2,6-dioxopiperidin-3-yl)isoindolin-1,3-dione and pharmaceutically acceptable salts thereof;

5-fluoro-2-(1-(2-methoxyethyl)-2,6-dioxopiperidin-3-yl)-isoindolin-1,3-dione and pharmaceutically acceptable salts thereof;

4-amino-2-(1-(2-methoxybutyl)-2,6-dioxopiperidin-3-yl)isoindolin-1,3-dione and pharmaceutically acceptable salts thereof;

4-hydroxy-2-(1-(2-methoxyethyl)-2,6-dioxopiperidin-3-yl)isoindolin-1,3-dione and pharmaceutically acceptable salts thereof;

4-methyl-2-(1-(2-methoxyethyl)-2,6-dioxopiperidin-3-yl)-isoindolin-1,3-dione and pharmaceutically acceptable salts thereof;

4-amino-5-methoxy-2-(1-(2-methoxyethyl)-2,6-dioxopiperidin-3-yl)-isoindolin-1,3-dione and pharmaceutically acceptable salts thereof;

4-amino-2-(1-(2-methoxyethyl)-2,6-dioxopiperidin-3-yl) isoindolin-1,3-dione and pharmaceutically acceptable salts thereof; and 4-amino-2-(1-(2-methoxypropyl)-2,6-dioxopiperidin-3-yl)isoindolin-1,3-dione and pharmaceutically acceptable salts thereof.

In another aspect, some embodiments disclose a piperidine-2,6-dione derivative of formula (II) and pharmaceutically acceptable salts thereof:

formula (II)

wherein, $R_4$ represents one or more substituents selected from the group consisting of H, halogen, —$C_{1-4}$alkyl, —$NH_2$, —$NHC_{1-4}$alkyl, —$N(C_{1-4}$alkyl$)_2$ and —$NHCOC_{1-4}$alkyl;

$R_5$ represents —$CH_2CH_2$—, —$CH_2CH_2CH_2$— or —$CH_2CH_2CH_2CH_2$—;

$R_6$ represents —S—, —SO—, —$SO_2$—, —NH— or —N($C_{1-4}$alkyl)-; and $R_7$ represents —H or —$C_{1-4}$alkyl.

Some embodiments disclose a piperidine-2,6-dione derivative of formula (II) and pharmaceutically acceptable salts thereof:

formula (II)

wherein, $R_4$ represents one or more substituents selected from the group consisting of —H, —F, —Cl, —Br, —OH, —$CH_3$, —$NHCH_3$, —$NHCH_2CH_3$, —$NH_2$, —$N(CH_3)_2$, —$N(CH_2CH_3)_2$, —$NHCOCH_3$ and —$NHCOCH_2CH_3$;

$R_5$ represents —$CH_2CH_2$—, —$CH_2CH_2CH_2$— or —$CH_2CH_2CH_2CH_2$—;

$R_6$ represents —S—, —SO—, —$SO_2$—, —NH— or —N($CH_3$)—; and $R_7$ represents —H, —$CH_3$ or —$CH_2CH_3$.

Some embodiments disclose a piperidine-2,6-dione derivative of formula (II) and pharmaceutically acceptable salts thereof:

formula (II)

wherein, $R_4$ represents —$NH_2$ or —$NHCOCH_3$;

$R_5$ represents —$CH_2CH_2$—, —$CH_2CH_2CH_2$— or —$CH_2CH_2CH_2CH_2$—;

$R_6$ represents —S—, —SO—, —$SO_2$—, —NH— or —N($CH_3$)—; and $R_7$ represents —H, —$CH_3$ or —$CH_2CH_3$.

Some embodiments disclose a piperidine-2,6-dione derivative of formula (II) and pharmaceutically acceptable salts thereof:

4-amino-2-(1-(2-methylthioethyl)-2,6-dioxopiperidin-3-yl)isoindolin-1,3-dione and pharmaceutically acceptable salts thereof;

4-amino-2-(1-(2-methylsulfinylethyl)-2,6-dioxopiperidin-3-yl)isoindolin-1,3-dione and pharmaceutically acceptable salts thereof; and 4-amino-2-(1-(2-methylsulfonylethyl)-2,6-dioxopiperidin-3-yl)isoindolin-1,3-dione and pharmaceutically acceptable salts thereof.

In yet another aspect, some embodiments disclose a piperidine-2,6-dione derivative of formula (III) and pharmaceutically acceptable salts thereof:

formula (III)

wherein, $R_8$ represents one or more substituents selected from the group consisting of H, halogen, —$C_{1-4}$alkyl, —$NH_2$, —$NHC_{1-4}$alkyl, —$N(C_{1-4}$alkyl) 2 and —$NHCOC_{1-4}$alkyl;

$R_9$ represents —$CH_2CH_2$—, —$CH_2CH_2CH_2$— or —$CH_2CH_2CH_2CH_2$—;

$R_{10}$ represents —O—, —S—, —SO—, —$SO_2$—, —NH— or —N($C_{1-4}$alkyl)-;

$R_{11}$ represents —H or —$C_{1-4}$alkyl; and $R_{12}$ represents halogen or —$C_{1-4}$alkyl.

Some embodiments disclose a piperidine-2,6-dione derivative of formula (III) and pharmaceutically acceptable salts thereof:

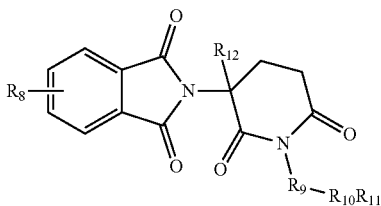

formula (III)

wherein,
$R_8$ represents one or more substituents selected from the group consisting of —H, —F, —Cl, —Br, —OH, —CH$_3$, —NHCH$_3$, —NHCH$_2$CH$_3$, —NH$_2$, —N(CH$_3$)$_2$, —N(CH$_2$CH$_3$)$_2$, —NHCOCH$_3$ and —NHCOCH$_2$CH$_3$;
$R_9$ represents —CH$_2$CH$_2$—, —CH$_2$CH$_2$CH$_2$— or —CH$_2$CH$_2$CH$_2$CH$_2$—;
$R_{10}$ represents —O—, —S—, —SO—, —SO$_2$—, —NH— or —N(CH$_3$)—;
$R_{11}$ represents —H, —CH$_3$ or —CH$_2$CH$_3$; and
$R_{12}$ represents halogen or —C$_{1-4}$alkyl.

Some embodiments disclose a piperidine-2,6-dione derivative of formula (III) and pharmaceutically acceptable salts thereof:

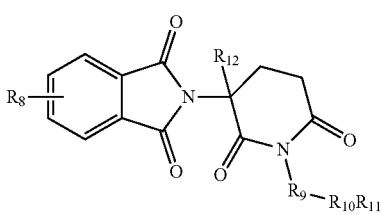

formula (III)

wherein,
$R_8$ represents —NH$_2$ or —NHCOCH$_3$;
$R_9$ represents —CH$_2$CH$_2$—, —CH$_2$CH$_2$CH$_2$— or —CH$_2$CH$_2$CH$_2$CH$_2$—;
$R_{10}$ represents —O—, —S—, —SO—, —SO$_2$—, —NH— or —N(CH$_3$)—;
$R_{11}$ represents —H, —CH$_3$ or —CH$_2$CH$_3$; and
$R_{12}$ represents halogen or —C$_{1-4}$alkyl.

Some embodiments disclose a piperidine-2,6-dione derivative of formula (III) and pharmaceutically acceptable salts thereof, which are selected from the group consisting of:
  4-amino-2-(1-(2-methoxyethyl)-3-fluoro-2,6-dioxopiperidin-3-yl)isoindolin-1,3-dione and pharmaceutically acceptable salts thereof; and
  4-amino-2-(1-(2-methoxyethyl)-3-methyl-2,6-dioxopiperidin-3-yl)isoindolin-1,3-dione and pharmaceutically acceptable salts thereof.

All the compounds of formula (I), formula (II) and formula (III) as mentioned above belong to piperidine-2,6-dione derivatives as mentioned herein.

Some embodiments disclose a piperidine-2,6-dione derivatives and pharmaceutically acceptable salts thereof, which are selected from the group consisting of:
  4-acetylamino-2-(1-(2-methoxyethyl)-2,6-dioxopiperidin-3-yl)isoindolin-1,3-dione and pharmaceutically acceptable salts thereof;
  4-methylamino-2-(1-(2-methoxyethyl)-2,6-dioxopiperidin-3-yl)isoindolin-1,3-dione and pharmaceutically acceptable salts thereof;
  4-dimethylamino-2-(1-(2-methoxyethyl)-2,6-dioxopiperidin-3-yl)isoindolin-1,3-dione and pharmaceutically acceptable salts thereof;
  4-fluoro-2-(1-(2-methoxyethyl)-2,6-dioxopiperidin-3-yl)isoindolin-1,3-dione and pharmaceutically acceptable salts thereof;
  4,5,6,7-tetrafluoro-2-(1-(2-methoxyethyl)-2,6-dioxopiperidin-3-yl)isoindolin-1,3-dione and pharmaceutically acceptable salts thereof;
  4-amino-2-(1-(2-hydroxyethyl)-2,6-dioxopiperidin-3-yl)isoindolin-1,3-dione and pharmaceutically acceptable salts thereof;
  5-amino-2-(1-(2-methoxyethyl)-2,6-dioxopiperidin-3-yl)isoindolin-1,3-dione and pharmaceutically acceptable salts thereof;
  4-amino-5-hydroxy-2-(1-(2-methoxyethyl)-2,6-dioxopiperidin-3-yl)isoindolin-1,3-dione and pharmaceutically acceptable salts thereof;
  4-amino-5-fluoro-2-(1-(2-methoxyethyl)-2,6-dioxopiperidin-3-yl)isoindolin-1,3-dione and pharmaceutically acceptable salts thereof;
  4-amino-7-hydroxy-2-(1-(2-methoxyethyl)-2,6-dioxopiperidin-3-yl)isoindolin-1,3-dione and pharmaceutically acceptable salts thereof;
  4-amino-2-(1-(2-methylthioethyl)-2,6-dioxopiperidin-3-yl)isoindolin-1,3-dione and pharmaceutically acceptable salts thereof;
  4-amino-2-(1-(2-methylsulfinylethyl)-2,6-dioxopiperidin-3-yl)isoindolin-1,3-dione and pharmaceutically acceptable salts thereof;
  4-amino-2-(1-(2-methylsulfonylethyl)-2,6-dioxopiperidin-3-yl)isoindolin-1,3-dione and pharmaceutically acceptable salts thereof;
  4-amino-2-(1-(2-methoxyethyl)-3-fluoro-2,6-dioxopiperidin-3-yl)isoindolin-1,3-dione and pharmaceutically acceptable salts thereof;
  4-amino-2-(1-(2-methoxyethyl)-3-methyl-2,6-dioxopiperidin-3-yl)isoindolin-1,3-dione and pharmaceutically acceptable salts thereof;
  4-acetylamino-2-(1-(2-methoxypropyl)-2,6-dioxopiperidin-3-yl)isoindolin-1,3-dione and pharmaceutically acceptable salts thereof;
  4-fluoro-2-(1-(2-methoxypropyl)-2,6-dioxopiperidin-3-yl)isoindolin-1,3-dione and pharmaceutically acceptable salts thereof;
  5-amino-2-(1-(2-methoxypropyl)-2,6-dioxopiperidin-3-yl)isoindolin-1,3-dione and pharmaceutically acceptable salts thereof;
  4-amino-2-(1-(2-ethoxyethyl)-2,6-dioxopiperidin-3-yl)isoindolin-1,3-dione and pharmaceutically acceptable salts thereof;
  4-fluoro-2-(1-(2-ethoxyethyl)-2,6-dioxopiperidin-3-yl)isoindolin-1,3-dione and pharmaceutically acceptable salts thereof;
  5-fluoro-2-(1-(2-methoxyethyl)-2,6-dioxopiperidin-3-yl)-isoindolin-1,3-dione and pharmaceutically acceptable salts thereof;
  4-amino-2-(1-(2-methoxybutyl)-2,6-dioxopiperidin-3-yl)isoindolin-1,3-dione and pharmaceutically acceptable salts thereof;
  4-hydroxy-2-(1-(2-methoxyethyl)-2,6-dioxopiperidin-3-yl)isoindolin-1,3-dione and pharmaceutically acceptable salts thereof;

4-methyl-2-(1-(2-methoxyethyl)-2,6-dioxopiperidin-3-yl)-isoindolin-1,3-dione and pharmaceutically acceptable salts thereof;

4-amino-5-methoxy-2-(1-(2-methoxyethyl)-2,6-dioxopiperidin-3-yl)-isoindolin-1,3-dione and pharmaceutically acceptable salts thereof;

4-amino-2-(1-(2-methoxyethyl)-2,6-dioxopiperidin-3-yl)isoindolin-1,3-dione and pharmaceutically acceptable salts thereof; and 4-amino-2-(1-(2-methoxypropyl)-2,6-dioxopiperidin-3-yl)isoindolin-1,3-dione and pharmaceutically acceptable salts thereof.

In still another aspect, some embodiments disclose a pharmaceutical composition comprising the piperidine-2,6-dione derivative or pharmaceutically acceptable salts thereof as disclosed herein, and a pharmaceutically acceptable carrier, diluent or excipient.

In yet another aspect, some embodiments disclose a method for treating ulcerative colitis, comprising administering a therapeutically effective amount of the piperidine-2,6-dione derivative or pharmaceutically acceptable salts thereof as disclosed herein, or a therapeutically effective amount of the pharmaceutical composition as disclosed herein to a subject in need thereof.

Some embodiments disclose a method for treating ulcerative colitis, comprising administering 1 mg-10 g of the piperidine-2,6-dione derivative or pharmaceutically acceptable salts thereof as disclosed herein to a subject in need thereof.

Some embodiments disclose a method for treating ulcerative colitis, comprising administering 10 mg-3000 mg of the piperidine-2,6-dione derivative or pharmaceutically acceptable salts thereof as disclosed herein to a subject in need thereof.

Some embodiments disclose a method for treating ulcerative colitis, comprising administering 100 mg-1000 mg of the piperidine-2,6-dione derivative or pharmaceutically acceptable salts thereof as disclosed herein to a subject in need thereof.

Some embodiments disclose a method for treating ulcerative colitis, comprising administering 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg or 1000 mg of the piperidine-2,6-dione derivative or pharmaceutically acceptable salts thereof as disclosed herein to a subject in need thereof.

Some embodiments disclose a method for treating ulcerative colitis, wherein the ulcerative colitis is mild ulcerative colitis, moderate ulcerative colitis, severe ulcerative colitis or ulcerative colitis in remission.

Some embodiments disclose a method for treating ulcerative colitis, wherein the subject in need thereof is a mammal.

Some embodiments disclose a method for treating ulcerative colitis, wherein the subject in need thereof is human.

Some embodiments disclose of a method of maintenance treatment of ulcerative colitis, comprising administering a therapeutically effective amount of the piperidine-2,6-dione derivative or pharmaceutically acceptable salts thereof as disclosed herein, or a therapeutically effective amount of the pharmaceutical composition as disclosed herein to a subject in need thereof.

Some embodiments disclose a method for treating ulcerative colitis, wherein the piperidine-2,6-dione derivative or pharmaceutically acceptable salts thereof as disclosed herein, or the pharmaceutical composition comprising the piperidine-2,6-dione derivative or pharmaceutically acceptable salts thereof as disclosed herein is administered orally.

Some embodiments disclose a method for treating ulcerative colitis, wherein the piperidine-2,6-dione derivative or pharmaceutically acceptable salts thereof as disclosed herein, or the pharmaceutical composition comprising the piperidine-2,6-dione derivative or pharmaceutically acceptable salts thereof as disclosed herein is administered orally in a solid or liquid formulation.

Exemplary examples of the solid formulation that can be used in the method for treating ulcerative colitis as disclosed herein comprise, but are not limited to, a tablet, capsule and sugar-coated pill.

Exemplary examples of the tablet that can be used in the method for treating ulcerative colitis as disclosed herein comprise, but are not limited to, a plain tablet, sugar-coated tablet and film-coated tablet.

Exemplary examples of the liquid formulation that can be used in the method for treating ulcerative colitis as disclosed herein comprise, but are not limited to, a solution and suspension.

In yet another aspect, some embodiments disclose a piperidine-2,6-dione derivative and pharmaceutically acceptable salts thereof for treating ulcerative colitis.

In still another aspect, some embodiments disclose a pharmaceutical composition for treating ulcerative colitis, comprising the piperidine-2,6-dione derivative or pharmaceutically acceptable salts thereof as disclosed herein, and a pharmaceutically acceptable carrier, diluent or excipient.

The piperidine-2,6-dione derivatives as disclosed herein have good therapeutical effects.

The piperidine-2,6-dione derivatives as disclosed herein have better safety.

The piperidine-2,6-dione derivatives as disclosed herein have better tolerance.

Pharmaceutical Compositions

Some embodiments disclose a pharmaceutical composition comprising the piperidine-2,6-dione derivative or pharmaceutically acceptable salts thereof as disclosed herein, and a pharmaceutically acceptable carrier, diluent or excipient.

In some embodiments, the route of administration of the piperidine-2,6-dione derivatives as disclosed herein to the mammals can be non-parenteral route.

In some embodiments, the route of administration of the piperidine-2,6-dione derivatives as disclosed herein to the mammals can be oral route.

In some embodiments, the route of administration of the piperidine-2,6-dione derivatives as disclosed herein to the mammals can be intrarectal route.

The piperidine-2,6-dione derivatives as described herein may be obtained in any suitable form such as tablet, capsule, powder, oral solution, suspension, rectal gel, rectal foam, rectal enema or suppository and the like. Exemplary examples of tablets comprise, but are not limited to, plain tablets, sugar-coated tablets and film-coated tablets.

Examples of a pharmaceutically acceptable carrier that can be used in the pharmaceutical composition of the present disclosure include, but are not limited to, any adjuvant, carrier, excipient, glidant, sweetening agent, diluent, preservative, dye/colorant, flavor enchancer, surfactant, wetting agent, dispersing agent, suspending agent, stabilizer, isosmotic agent, solvent or emulsifier, which has been approved by the United States Food and Drug Administration as being acceptable for use in humans or animals. Acceptable carriers or diluents for therapeutic use are well-known in the art, and are described, for example, in Remington's Pharmaceutical Sciences, 18th Ed., Mack Publishing Co., Easton, Pa. (1990), which is incorporated herein by reference in its entirety.

The pharmaceutical compositions of the present disclosure may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. The route of administration can be non-parenteral route, oral route and intrarectal route. The dosage administered will be dependent upon the age, health, and weight of the recipient, kind of concurrent treatment, if any, frequency of treatment, and the nature of the effect desired.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art.

Particularly suitable for oral use are ordinary tablets (plain tablets), sugar-coated tablet, film-coated tablets, pills, coated tablets, capsules, powders, granules, syrups, juices or drops, suitable for rectal use are suppositories, suitable for parenteral use are solutions, or oil-based or aqueous solutions, furthermore suspensions, emulsions or implants, and suitable for topical use are ointments, creams or powders. The compounds of the present disclosure may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

In some embodiments, a pharmaceutical composition of the present disclosure is formulated as tablet, solution, granule, patch, ointment, capsule, aerosol or suppository administered via parenteral, transdermal, mucosa, nasal, buccal, sublingual or oral route.

Preservatives, stabilizers, dyes, sweeteners, flavoring agents, fragrances, and the like, may be provided in the pharmaceutical composition. For example, sodium benzoate, ascorbic acid and esters of p-hydroxybenzoic acid may be added as preservatives. Furthermore, antioxidants and suspending agents may be used.

In various embodiments, alcohols, esters, sulfating aliphatic alcohols, and the like may be used as surfactants; sucrose, glucose, lactose, starch, crystalline cellulose, mannitol, light anhydrous silicate, magnesium aluminate, methyl magnesium silicate aluminate, synthetic aluminum silicate, calcium carbonate, calcium bicarbonate, calcium hydrogenphosphate, calcium hydroxymethyl cellulose and the like may be used as excipients; magnesium stearate, talc, hardened oil may be used as smoothing agents; coconut oil, olive oil, sesame oil, peanut oil, soybean may be used as suspending agents or lubricants; cellulose acetate phthalate as a derivative of a carbohydrate such as cellulose or sugar, or methylacetate-metharylate copolymer as a derivative of polyethylene may be used as suspending agents; and plasticizers such as ester phthalates and the like may be used as suspending agents.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal or intraocular injections. The compound can be administered in sustained or controlled release dosage forms, including depot injections, osmotic pumps, pills, transdermal (including electromigrating) patches, and the like for prolonged and/or timed, pulsed administration at a predetermined rate.

Pharmaceutical compositions of the present disclosure may be manufactured in manner that is itself known, for example, by means of conventional mixing, dissolving, granulating, dragee-making, levigating, emulsifying, encapsulating, entrapping, or tabletting processes.

Pharmaceutical compositions for use in accordance with the present disclosure thus may be formulated by a conventional manner using one or more physiologically acceptable carriers comprising excipienst and auxiliaries which facilitate processing the active compounds into preparation which can be used pharmaceutically. Proper formulation is dependent on the route of administration chosen. Any of the well-known techniques, carriers and excipients may be used as suitable and as understood in the art.

Injectables can be prepared in conventional forms, either as liquid solutions or suspensions, solid forms suitable for solution or suspension in liquid prior to injection, or as emulsions. Suitable excipients are, for example, water, saline, glucose, mannitol, lactose, lecithin, albumin, sodium glutamate, cysteine hydrochloride, and the like. Furthermore, if desired, the injectable pharmaceutical compositions may contain minor amounts of nontoxic auxiliary substances, such as wetting agents, pH buffering agents, and the like. Physiologically compatible buffers include, but are not limited to, Hank's solution, Ringer's solution or physiological saline buffer. If desired, absorption enhancing preparations (such as liposomes) may be used.

For oral administration, the compound can be formulated readily by combining the active compound with pharmaceutically acceptable carriers well known in the art. Such carriers enable the compound of the disclosure to be formulated as tablets, pills, dragees, capsules, liquids, gels, syrups, ointments, suspensions, and the like, for oral ingestion by a patient to be treated. Pharmaceutical preparation for oral use can be obtained by combining the active compound with solid excipient, optionally grinding a resultant mixture, and processing the mixture of granules, after adding suitable auxiliaries, if desired, to obtain tablets or dragee cores. Suitable excipients are, in particular, fillers such as sugars, including lactose, saccharose, mannitol or sorbitol; cellulose preparations such as, for example, maize starch, wheat starch, rice starch, potato starch, gelatin, gum tragacanth, methylcellulose, hydroxypropyl methylcellulose, sodium carboxymethylcellulose, and/or polyvinylpyrrolidone (PVP). If desired, disintegrating agents may be added, such as the crosslinked polyvinylpyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solution, and suitable organic solvents or solvent mixtures. Dyestuffs or pigments may be added into the tablets or dagree coatings for identification or to characterizing different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solution, and suitable organic solvents or solvent mixtures.

Pharmaceutical preparations which can be used orally include push-fit capsules made of gelatin, as well as soft, sealed capsules made of gelatin and a plasticizer such as glycerol or sorbitol. The push-fit capsules can contain active ingredients in admixture with filler such as sugar, binders such as starches, and/or lubricants such as talc or magnesium stearate and, optionally, stabilizers. In soft capsules, the active ingredients may be dissolved or suspended in suitable liquids, such as fatty oil, liquid paraffin, or liquid polyethylene glycols. Furthermore, stabilizers may be added. All formulations for oral administration should be in dosages suitable for such administration.

In some embodiments, the pharmaceutical composition of the present disclosure may comprise 0.1%-95% of the piperidine-2,6-dione derivatives as disclosed herein.

In some embodiments, the pharmaceutical composition of the present disclosure may comprise 1%-70% of the piperidine-2,6-dione derivatives as disclosed herein.

Under any circumstances, the composition or formulation to be administered may comprise some amount of the piperidine-2,6-dione derivatives as disclosed herein, which is effective to treat the disease/condition of a study subject to be treated.

Methods of Administration

At least one of the compounds of the present disclosure or the pharmaceutical compositions comprising at least one of the compounds of the present disclosure may be administered to the patient by any suitable means and/or by any means that topically delivers the compounds of the present disclosure. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of the present disclosure into contact with living tissue.

The most suitable route depends on the nature and severity of the condition to be treated. A person having ordinary skill in the art also knows determination of methods of administration (buccal, intravenous, inhalation subcutaneous, rectal and the like), dosage form, suitable pharmaceutical excipients and other events regarding delivering the compound to a subject in need thereof.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages may be between about 10 microgram/kg and 1000 mg/kg body weight, in some embodiments, between about 100 microgram/kg and 300 mg/kg body weight. Alternatively dosages may be based and calculated upon the surface area of the patient, as understood by those of skill in the art.

The exact formulation, route of administration and dosage for the pharmaceutical compositions of the present disclosure can be chosen by the individual physician in view of the patient's condition. Typically, the dose range of the composition administered to the patient can be from about 0.5 to 1000 mg/Kg of the patient's body weight. The dosage may be a single one or a series of two or more given in the course of one or more days, as is needed by the patient. In instances where human dosages for compounds have been established for at least sonic condition, the present disclosure will use those same dosages, or dosages that are between about 0.1% and 500%, in some embodiments, between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, in some embodiments, between 1 mg and 2000 mg, e.g. 5 to 1500 mg. In other embodiments, an intravenous, subcutaneous, or intramuscular dose of each active ingredient of between 0.01 mg and 1.000 mg, in some embodiments, between 0.1 mg and 1000 mg, e.g. 1 to 800 mg is used. In cases of administration of a pharmaceutically acceptable salt, dosages may be calculated as the free base. In some embodiments, the composition is administered 1 to 4 times per day. Alternatively the compositions of the disclosure may be administered by continuous intravenous infusion, in some embodiments, at a dose of each active ingredient up to 2000 mg per day. As will be understood by those of skill in the art, in certain situations it may be necessary to administer the compounds disclosed herein in amounts that exceed, or even far exceed, the above-stated dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC), The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, in some embodiments, between 30-90% and in some embodiments, between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and in some embodiments, human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but, not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. S uch notice, for example, may be the labeling approved by the U.S. Food and Drug Administration for prescription drugs, or the approved product insert. Compositions comprising a compound of the disclosure formulated in a compatible pharmaceutical carrier may also be prepared, placed in an appropriate container, and labeled for treatment of an indicated condition.

EXAMPLES

The following abbreviations were used in the discussion, examples and preparations.

LPS: lipopolysaccharide;
PBS: phosphate buffered saline;
Tween-20
PBST: 0.05% of Tween-20 in phosphate buffered saline;
HRP: horseradish peroxidase;
TMB: 3,3',5,5'-tetramethylbenzidine;
DSS: dextra sulfate sodium;
5-ASA: 5-aminosalicylic acid;
CMC-Na: sodium carboxymethyl cellulose;
DNBS: dinitrobenzenesulfonic acid;
1% C MC-Na: 1% (weight/volume) of CMC-Na in water;
1.6% DSS: 1.6% (weight/volume) of DSS in water;
0.9% DSS: 0.9% (weight/volume) of DSS in water;
mg/Kg: milligram/kilogram;
mg/Kg/d: milligram/kilogram/day;
mL/Kg: milliliter/kilogram;
cm: centimeter;
Mean±SD: Mean±standard deviation;
30% ethanol: 30% (volume/volume) of ethanol in water;
$cm^2$: square centimeter;
U/mg: unit/milligram;
g: gram;
mmol: millimole;
mol/L: mole/liter;
i.g: intragastric administration;
mL: milliliter;
MPO: myeloperoxidase;
μL: microliter;
nm: nanometer;
s: second;
OD value: optical density value;
μm: micron;
Qd, QD, Q.D or qd: once a day.

The following instruments or devices may be used in the experiments:

| Instruments | Type | Company |
| --- | --- | --- |
| Animal Endoscopy | VET-6011 | Shanghai Aohua Endoscopy Co., Ltd. |
| FullyAutomated Biochemical Analyzer | Cobas c 311 | Roche |
| ELIASA | Multiskan GO | Thermo Scientific |
| ELIASA | Model 680 | Biorad |
| Microplate Washer | Model 1575 | Biorad |
| Animal Fixator | Chinese Patent No. ZL 200800089997.7 | Suzhou Monkey Animal Experimental Equipment Technology Co., Ltd. |
| High-speed Centrifuge | TGL-16B | Shanghai Anting Scientific Instrument Factory |
| Triple Quadrupole Mass Spectrometer (TQMS) | API3000 | Applied Biosystems |
| High Performance Liquid Chromatography (HPLC) | LC-20A | Shimadzu Corporation |
| Vortex Mixer | QL901 | Haimen Kylin-Bell Lab Instruments Co., Ltd. |
| Low-temperature High-speed Centrifuge | Heraeus Multifuge X3R | Thermo Scientific |
| Fully Automated Vacuum Processor | Leica ASP200S | Leica Instruments Germany GmbH |
| Embedding Machine | Leica EG1150H + C | Leica Instruments Germany GmbH |
| Manual Microtome | Leica RM2235 | Leica Instruments Germany GmbH |
| Water Bath for Paraffin Sections | Leica-HI1210 | Leica Instruments Germany GmbH |
| Fully Automated Stainer | Leica-ST5020 | Leica Instruments Germany GmbH |
| Fully Automated Glass Coverslipper | Leica CV5030 | Leica Instruments Germany GmbH |
| Liquid chromatography tandem-mass spectrometry (LC-MS/MS) | AUQUITY UPLC-Xevo TQD | Waters |
| Nuclear magnetic resonance spectrometer | Bruker AVANCE III 400 MHz NMR | Bruker |

The Chinese patent No. ZL200510013292.3 discloses the preparation process of 4-amino-2-(1-(2-methoxyethyl)-2,6-dioxopiperidin-3-yl)isoindolin-1,3-dione, which is incorporated herein by reference in its entirety.

Example 1

Preparation of 4-acetylamino-2-(1-(2-methoxyethyl)-2,6-dioxopiperidin-3-yl)isoindolin-1,3-dione 4-amino-2-(1-(2-methoxyethyl)-2,6-dioxopiperidin-3-yl)isoindolin-1,3-dione was prepared in accordance with the process disclosed in the Chinese patent No. ZL200510013292.3.

In dichloromethane (DCM) (30 mL) was dissolved 4-amino-2-(1-(2-methoxyethyl)-2,6-dioxopiperidin-3-yl)isoindolin-1,3-dione (3.0 g). Triethylamine (TEA) (2.75 g, 3.77 mL) and 4-dimethylaminopyridine (DMAP) (0.126 g) were added into the solution. The air was replaced with argon. The temperature of the reaction system was lowered to 0° C. To the reaction system was added acetyl chloride (4.59 g, 4.16 mL) with stirring. The temperature of the reaction system was slowly heated to the room temperature until the reaction was complete. To the reaction solution was added water (60 mL) to quench the reaction. The solution was extracted once with dichloromethane. The organic phase was washed once with saturated aqueous solution of sodium chloride, dried over anhydrous magnesium sulfate and filtered. The solvent was evaporated under reduced pressure to give a crude product. The crude product was purified with silica gel column chromatography to give a solid product (1.8 g). The solid product was dissolved in dichloromethane. To the solution was added dropwise diethyl ether to separate out a product. The resultant product was dissolved in dichloromethane. To the solution was added diethyl ether to separate out a product. The resultant product was dried under reduced pressure to give the title compound of Example 1 as a white solid (1.3 g) (HPLC purity: 98.06%). Yield: 38.3%.

$^1$HNMR (deuterated chloroform (CDCl$_3$), 400 MHz) δ 9.411(bs, 1H), 8.823-8.802(d, 1H), 7.730-7.690(dd, 1H), 7.557-7.537(dd, 1H), 4.995-4.950(m, 1H), 4.146-4.001(m, 2H), 3.555-3.521(m, 2H), 3.345(s, 3H), 3.048-2.956(m, 1H), 2.848-2.719(m, 2H), 2.267(s, 3H), 2.186-2.086(m, 1H). MS(m/e): 374.2 1(M+H$^+$).

Example 2

Preparation of 4-methylamino-2-(1-(2-methoxyethyl)-2,6-dioxopiperidin-3-yl)isoindolin-1,3-dione To a reaction flask were added 4-amino-2-(1-(2-methoxyethyl)-2,6-dioxopiperidin-3-yl)isoindolin-1,3-dione (4.0 g), di-tert-butyl dicarbonate (10.528 g) and 4-dimethylaminopyridine (0.147 g). To the reaction flask was added tetrahydrofuran (40 mL). The solution was stirred at the room temperature overnight. The reaction solution was concentrated under reduced pressure to give a crude product. The crude product was purified with silica gel column chromatography to give 4-di-BOC-amino-2-(1-(2-methoxyethyl)-2,6-dioxopiperidin-3-yl)-isoindolin-1,3-dione (3.3 g) as a white solid. Yield: 74.1%. MS (m/e): 554.40 (M+Na$^+$).

4-di-BOC-amino-2-(1-(2-methoxyethyl)-2,6-dioxopiperidin-3-yl)-isoindolin-1,3-dione (2.05 g) was dissolved in dichloromethane (600 mL). To the solution was added tetrahydrofuran (3 mL). The reaction solution was stirred at the room temperature until the reaction was complete. To the resultant solution was added saturated aqueous solution of sodium bicarbonate to quench the reaction. The solution was separated. The organic phase was dried over anhydrous magnesium sulfate and filtered to give a filtrate. The filtrate was concentrated under reduced pressure to give 4-BOC-amino-2-(1-(2-methoxyethyl)-2,6-dioxopiperidin-3-yl)-isoindolin-1,3-dione (1.66 g) (HPLC purity: 98.62%). Yield: 100%. MS (m/e): 454.29 (M+Na$^+$).

To a reaction flask were added 4-Boc-amino-2-(1-(2-methoxyethyl)-2,6-dioxopiperidin-3-yl)-isoindolin-1,3-dione (3.0 g), methyl iodide (2.96 g) and potassium carbonate (2.88 g). To the reaction flask was added N,N-dimethylformamide (30 mL). The reaction solution was stirred at the room temperature overnight. The reaction solution was diluted with dichloromethane (100 mL). The organic phase was washed with water. The aqueous phase was extracted with dichloromethane. The organic phases were combined. The combined organic phase was washed with saturated aqueous solution of sodium chloride, dried over anhydrous magnesium sulfate and filtered to give a filtrate. The filtrate was concentrated under reduced pressure to give a crude product. The crude product was purified with silica gel column chromatography to give 4-BOC-methylamino-2-(1-(2-methoxyethyl)-2,6-dioxopiperidin-3-yl)-isoindolin-1,3-dione as a yellow oil (2.91 g) (HPLC purity: 96.43%). Yield: 94.0%. MS (m/e): 468.31 (M+Na$^+$).

4-BOC-methylamino-2-(1-(2-methoxyethyl)-2,6-dioxopiperidin-3-yl)-isoindolin-1,3-dione (2.9 g) was dissolved in dichloromethane (30 mL). To the solution was added tetrahydrofuran (6 mL). The reaction solution was stirred at the room temperature over 2 hours. The resultant solution was concentrated under reduced pressure to give a crude product. The crude product was dissolved in methyl tert-butyl ether (35 mL). The solution was stirred overnight to separate out a yellow solid product and fitered. The product was dried under reduced pressure to give the title compound as a yellow solid (1.83 g) (HPLC purity: 98.62%). Yield: 81.6%.

$^1$HNMR (CDCl$_3$, 400 MHz) δ 7.538-7.499 (dd, 1H), 7.112-7.094 (d, 1H), 6.887-6.866 (d, 1H), 4.949-4.904 (m, 1H), 4.122-3.999 (m, 2H), 3.543-3.510 (m, 2H), 3.341 (s, 3H), 2.989-2.950 (m, 1H), 2.981 (s, 3H), 2.820-2.700 (m, 2H), 2.115-2.060 (m, 1H). MS (m/e): 346.24 (M+H$^+$).

Example 3

Preparation of 4-dimethylamino-2-(1-(2-methoxyethyl)-2,6-dioxopiperidin-3-yl)isoindolin-1,3-dione To a pressure-resistant reaction tube were added 4-amino-2-(1-(2-methoxyethyl)-2,6-dioxopiperidin-3-yl)isoindolin-1,3-dione (3.0 g), methyl iodide (14.2 g) and potassium carbonate (6.25 g). To the pressure-resistant reaction tube was added N,N-dimethylformamide (20 mL). The reaction tube was sealed and heated to 80° C. in an oil bath. The reaction solution was stirred over 80 hours. The resultant solution was diluted with dichloromethane (200 mL) and filtered to give a filtrate. The filtrate was concentrated under reduced pressure to give a black oily crude product. The crude product was purified with silica gel column chromatography to give a brown solid (3.2 g). The brown solid was dissolved in ethyl acetate (20 mL) and stirred overnight. The resultant solution was filtered to give a solid. The solid was dried under reduced pressure to give the title compound as a yellow powdery solid (1.67 g) (HPLC purity: 97.22%). Yield: 51.4%.

$^1$HNMR (CDCl$_3$, 400 MHz) δ 7.543-7.504 (dd, 1H), 7.308-7.287 (d, 1H), 7.121-7.100 (d, 1H), 5.004-4.959 (m, 1H), 4.115-3.999 (m, 2H), 3.537-3.507 (m, 2H), 3.337 (s, 3H), 3.108 (s, 6H), 2.982-2.944 (m, 1H), 2.803-2.751 (m, 2H), 2.094-2.079 (m, 1H). MS (m/e): 360.27 (M+H$^+$).

Example 4

Preparation of 4-fluoro-2-(1-(2-methoxyethyl)-2,6-dioxopiperidin-3-yl)isoindolin-1,3-dione To a reaction flask were added 1-(2-methoxyethyl)-3-benzyloxyamido-2,6-piperidinedione acetate (35 g), palladium on carbon (3.5 g, content of palladium: 10%) and acetic acid (13 mL). The air in the flask was replaced with hydrogen three times. The reaction solution was stirred at the room temperature over 72 hours. The resultant solution was filtered to give a filtrate, which was directly used in the next step.

To a reaction flask were added the above filtrate (comprising 2.0 g (calculated) of 1-(2-methoxyethyl)-3-amino-2,6-piperidinedione acetate), 3-fluorophthalic anhydride (1.35 g), sodium acetate (0.67 g) and acetic acid (43 mL). The solution was heated to 140° C. in an oil bath and stirred to react over 5 hours. The resultant solution was concentrated under reduced pressure to give a black crude product. The crude product was purified with silica gel column chromatography to give the title compound as a white solid (1.56 g) (HPLC purity: 99.88%). Yield: 57.4%.

$^1$HNMR (CDCl$_3$, 400 MHz) δ 7.796-7.746 (m, 1H), 7.717-7.700 (d, 1H), 7.447-7.403 (m, 1H), 5.028-4.982 (m, 1H), 4.127-3.998 (m, 2H), 3.541-3.510 (m, 2H), 3.340 (s, 3H), 3.019-2.951 (m, 1H), 2.895-2.739 (m, 2H), 2.171-2.085 (m, 1H). MS (m/e): 357.19 (M+Na$^+$).

Example 5

Preparation of 4,5,6,7-tetrafluoro-2-(1-(2-methoxyethyl)-2,6-dioxopiperidin-3-yl)isoindolin-1,3-dione Using the preparation process in Example 4, 3,4,5,6-tetrafluorophthalic anhydride and 1-(2-methoxyethyl)-3-amino-2,6-piperidinedione acetate were reacted to give the title compound as a white solid (2.93 g) (HPLC purity: 97.58%). Yield: 78.6%.

$^1$HNMR (CDCl$_3$, 400 MHz) δ 4.999-4.953 (m, 1H), 4.118-3.984 (m, 2H), 3.530-3.500 (m, 2H), 3.333 (s, 3H), 3.029-2.991 (m, 1H), 2.803-2.764 (m, 2H), 2.136-2.117 (m, 1H). MS (m/e): 389.22 (M+H$^+$).

Example 6

Preparation of 4-amino-2-(1-(2-hydroxyethyl)-2,6-dioxopiperidin-3-yl)isoindolin-1,3-dione To a reaction flask were added 3-amino-N-(2,6-dioxo-3-piperidinyl) phthalimide (3.5 g), 2-bromoethanol (4.8 g), potassium carbonate (1.77 g) and N,N-dimethylformamide (35 mL). The reaction flask was heated to 40° C. in an oil bath. The reaction solution was stirred over 80 hours. The reaction system was cooled to the room temperature. To the reaction system was added water (80 mL) to quench the reaction. To the solution was added ethyl acetate. The resultant solution was stirred to separate out a solid. The resultant mixture was filtered under reduced pressure. The filter cake was discarded and the filtrate was collected and separated. The aqueous phase was back-extracted with ethyl acetate four times. The organic phases were combined. The combined organic phase was washed with saturated aqueous solution of sodium chloride, dried over anhydrous magnesium sulfate and filtered. The organic phase was concentrated under reduced pressure to give a crude product. The crude product was purified with silica gel column chromatography to give the title compound as a yellow solid (2.0 g) (HPLC purity: 95.53%). Yield: 49.2%.

$^1$HNMR (CDCl$_3$, 400 MHzz) δ 7.457-7.419 (t, 1H), 7.176-7.158 (d, 1H), 6.886-6.865 (d, 1H), 4.990-4.945 (m, 1H), 4.135-4.065 (m, 2H), 3.813-3.785 (m, 2H), 3.006-2.966 (m, 1H), 2.829-2.714 (m, 2H), 2.153-2.114 (m, 1H). MS (m/e): 340.18 (M+Na$^+$).

Example 7

Preparation of 5-amino-2-(1-(2-methoxyethyl)-2,6-dioxopiperidin-3-yl)isoindolin-1,3-dione Using the preparation process in Example 4, 4-nitrophthalic anhydride and 1-(2-methoxyethyl)-3-amino-2,6-piperidinedione acetate were reacted to give 5-nitro-2-(1-(2-methoxyethyl)-2,6-dioxopiperidin-3-yl)-isoindolin-1,3-dione as a white solid (2.8 g) (HPLC purity: 99.62%). Yield: 54.5. MS (m/e): 384.18 (M+Na$^+$).

To a reaction flask were added 5-nitro-2-(1-(2-methoxyethyl)-2,6-dioxopiperidin-3-yl)-isoindolin-1,3-dione (2.6 g), palladium on carbon (0.26 g) and tetrahydrofuran (30 mL). The air in the flask was replaced with hydrogen three times. The reaction solution was stirred at the room temperature over 20 hours until the reaction was complete. The resultant solution was filtered to give a filtrate. The filtrate was concentrated under reduced pressure with water pump to give a crude product. The crude product was dissolved and purified with ethyl acetate to give the title compound as a yellow solid (1.56 g) (HPLC purity: 95.74%). Yield: 65.4%.

$^1$HNMR (CDCl$_3$, 400 MHz) δ 7.607-7.587 (d, 1H), 7.012-7.007 (d, 1H), 6.846-6.820 (dd, 1H), 4.970-4.925 (m, 1H), 4.135-3.982 (m, 2H), 3.540-3.509 (m, 2H), 3.340 (s, 3H), 3.024-2.903 (m, 1H), 2.829-2.710 (m, 2H), 2.117-2.062 (m, 1H). MS (m/e): 354.22 (M+Na$^+$).

Example 8

Preparation of 4-amino-5-hydroxy-2-(1-(2-methoxyethyl)-2,6-dioxopiperidin-3-yl)isoindolin-1,3-dione To a reaction flask were added 4-hydroxyphthalate dimethyl (125 g) and concentrated sulfuric acid (600 mL). The solution was stirred and cooled to 0° C. To the reaction system was slowly added dropwise fuming nitric acid (39.44 g). The temperature of the reaction system was controled to be below 5° C. The addition of fuming nitric acid was complete in about 1 hour. The ice bath was removed. The solution was heated to the room temperature and stirred over 22 hours until the reaction was complete. The resultant solution was slowly poured into ice water to quench the reaction. The aqueous phase was extracted with ethyl acetate five times. The organic phases were combined. The combined organic phase was dried over anhydrous magnesium sulfate and filtered. The filtrate was collected and concentrated under reduced pressure with water pump and oil pump successively to give 4-hydroxy-3-nitrophthalate dimethyl (169 g) (HPLC purity: 36.54%), which was directly used in the next step. MS (m/e): 254.07 (M–H)$^-$.

To a reaction flask were added 4-hydroxy-3-nitrophthalate dimethyl (164 g), benzyl bromide (135.9 g), potassium carbonate (400 g) and acetone (1730 mL). The reaction flask was heated to 70° C. in an oil bath. The solution was stirred over 23 hours until the reaction was complete. The reaction system was cooled to the room temperature and concentrated under reduced pressure. The filter cake was washed with dichloromethane. The filtrate was collected and concentrated under reduced pressure. To the concentrate were added dichloromethane (2000 mL) and saturated aqueous solution of sodium chloride (1000 mL). The resultant solution was extracted. The organic phase was dried over anhydrous magnesium sulfate, filtered and concentrated under reduced pressure to give a yellow solid crude product. The crude product was recrystallized and purified with ethyl acetate to give 4-benzyloxy-3-nitrophthalate dimethyl as a white solid (40 g) (HPLC purity: 96.96%). Yield: 18.1%. MS (m/e): 346.14 (M+H$^+$).

To a reaction flask were added 4-benzyloxy-3-nitrophthalate dimethyl (30 g) and ethanol (300 mL). To the reaction flask was added preformulated aqueous solution of sodium hydroxide (24 g of sodium hydroxide in 300 mL of water). The reaction flask was heated to 70° C. in an oil bath. The solution was stirred over 7 hours until the reaction was complete. The reaction system was cooled to the room temperature and concentrated under reduced pressure to evaporate most of ethanol. To the concentrate was added 4 N hydrochloric acid at the room temperature until the pH of the solution was adjusted to 2 such that a lot of white solids were separated out. The resultant mixture was filtered under reduced pressure. The filter cake was collected and dried under reduced pressure with oil pump to give 4-benzyloxy-3-nitrophthalic acid as a white solid (27.5 g) (HPLC purity: 99.55%). Yield: 100%. MS (m/e): 316.15 (M–H)$^-$.

To a reaction flask were added 4-benzyloxy-3-nitrophthalic acid (19.1 g) and acetic anhydride (120 mL). The flask was heated to 140° C. in an oil bath. The solution was stirred over 6 hours. The reaction system was cooled to the room temperature. The resultant solution was concentrated under reduced pressure to give a crude product. The crude product was dissolved and purified with methyl tert-butyl ether and n-hexane to give 4-benzyloxy-3-nitrophthalic anhydride as a brown solid (16.8 g). Yield: 93.3%.

Using the preparation process in Example 4, 4-benzyloxy-3-nitrophthalic anhydride and 1-(2-methoxyethyl)-3-amino-2,6-piperidinedione acetate were reacted to prepare 4-nitro-5-benzyloxy-2-(1-(2-methoxyethyl)-2,6-dioxopiperidin-3-yl)-isoindolin-1,3-dione as a white solid (22.3 g) (HPLC purity: 99.69%). Yield: 85.0%. MS (m/e): 468.22 (M+H$^+$).

Using the preparation process in Example 7, 4-nitro-5-benzyloxy-2-(1-(2-methoxyethyl)-2,6-dioxopiperidin-3-yl)-isoindolin-1,3-dione was used to give the title compound as a yellow solid (18.4 g) (HPLC purity: 99.03%). Yield: 86.8%.

$^1$HNMR (dimethyl sulfoxide (DMSO), 400 MHz) δ 10.820 (s, 1H), 6.974-6.955 (d, 1H), 6.915-6.896 (d, 1H), 5.936-5.935 (bs, 2H), 5.099-5.053 (q, 1H), 3.917-3.730 (m, 2H), 3.363-3.331 (t, 2H), 3.217 (s, 3H), 3.002-2.911 (m, 1H), 2.762-2.702 (m, 1H), 2.560-2.450 (m, 1H), 2.027-1.963 (m, 1H). MS (m/e): 348.17 (M+H$^+$).

Example 9

Preparation of 4-amino-5-fluoro-2-(1-(2-methoxyethyl)-2,6-dioxopiperidin-3-yl)isoindolin-1,3-dione To a reaction flask were added 4-fluorophthalic acid (1.0 g) and concentrated sulfuric acid (5 mL). The solution was stirred and cooled to 0° C. To the reaction system was slowly added dropwise concentrated nitric acid (1.05 g, content: 65%). After the addition was complete, the resultant solution was heated to 80° C. in an oil bath. The solution was stirred over 7 hours. HPLC was used to monitor the reaction until the reaction was complete. The resultant solution was slowly poured into ice water (20 g) to quench the reaction. The aqueous phase was extracted with ethyl acetate. The organic phases were combined. The combined organic phase was washed with saturated aqueous solution of sodium chloride, dried over anhydrous magnesium sulfate and filtered. The filtrate was collected and concentrated under reduced pressure with water pump and oil pump successively to give a yellow solid (1.3 g), which was directly used in the next step.

To a reaction flask was added thionyl chloride (5 mL). The reaction system was heated to 90° C. in an oil bath and stirred over 11 hours. The reaction system was then cooled to the room temperature. The reaction solution was concentrated under reduced pressure with water pump to give a crude product as a yellow oil (0.56 g), which was directly used in the next step.

Using the preparation process in Example 4, 4-fluoro-3-nitrophthalic anhydride and 1-(2-methoxyethyl)-3-amino-2,6-piperidinedione acetate were reacted to prepare 5-fluoro-4-nitro-2-(1-(2-methoxyethyl)-2,6-dioxopiperidin-3-yl)-isoindolin-1,3-dione as a black solid (0.3 g) (HPLC purity: 90.63%). MS (m/e): 380.21 (M+H$^+$).

Using the preparation process in Example 7, 5-fluoro-4-nitro-2-(1-(2-methoxyethyl)-2,6-dioxopiperidin-3-yl)-isoindolin-1,3-dione was used to give the title compound as a yellow solid (0.137 g) (HPLC purity: 97.59%). Yield: 57.2%.

$^1$HNMR (CDCl$_3$, 400 MHz) δ 7.256-7.208 (dd, 1H), 7.158-7.129 (dd, 1H), 5.269 (bs, 2H), 4.959-4.914 (m, 1H), 4.140-3.988 (m, 2H), 3.544-3.512 (m, 2H), 3.341 (s, 3H), 3.000-2.961 (m, 1H), 2.795-2.745 (m, 2H), 2.121-2.081 (m, 1H). MS (m/e): 350.2 (M+H$^+$).

Example 10

Preparation of 4-amino-7-hydroxy-2-(1-(2-methoxyethyl)-2,6-dioxopiperidin-3-yl)isoindolin-1,3-dione 4-BOC-amino-7-hydroxyphthalate dimethyl was prepared in accordance with Journal of Organic Chemistry, 62(12), 4088-4096; 1997.

To a reaction flask were added 3-BOC-amino-6-hydroxyphthalate dimethyl (3.0 g), 1-(2-methoxyethyl)-3-amino-2,6-piperidinedione acetate (4.5 g) and pyridine (60 mL). The reaction flask was heated to 100° C. in an oil bath. The reaction solution was stirred over 40 hours and then cooled to the room temperature. The resultant solution was concentrated to give a crude product. The crude product was purified with silica gel column chromatography to give 4-BOC-amino-7-hydroxy-2-(1-(2-methoxyethyl)-2,6-dioxopiperidin-3-yl)-isoindolin-1,3-dione as a yellow solid (2.35 g) (HPLC purity: 95.96%). Yield: 48.8%. MS (m/e): 470.28 (M+Na$^+$).

4-BOC-amino-7-hydroxy-2-(1-(2-methoxyethyl)-2,6-dioxopiperidin-3-yl)-isoindolin-1,3-dione (2.25 g) was dissolved in dichloromethane (20 mL). To the solution was added tetrahydrofuran (4 mL). The resultant solution was stirred at the room temperature over 6 hours until the reaction was complete. The solution was concentrated under reduced pressure to give a crude product. The crude product was dissolved and purified with methyl tert-butyl ether to give the title compound as brown solid (1.413 g) (HPLC purity: 95.35%). Yield: 77.4%.

$^1$HNMR (CDCl$_3$, 400 MHz) δ 7.020-6.998 (d, 1H), 6.858-6.835 (d, 1H), 4.934-4.889 (m, 1H), 4.145-3.995(m, 2H), 3.555-3.521 (m, 2H), 3.346 (s, 3H), 3.031-2.926 (m, 1H), 2.827-2.742 (m, 2H), 2.140-2.059 (m, 1H). MS (m/e): 348.22 (M+H$^+$).

Example 11

Preparation of 4-amino-2-(1-(2-methylthioethyl)-2,6-dioxopiperidin-3-yl)isoindolin-1,3-dione To a reaction flask were added 3-amino-N-(2,6-dioxo-3-piperidinyl) phthalimide (2.5 g), 2-chloroethyl methyl sulfide (2.55 g), potassium carbonate (3.8 g), sodium iodide (0.28 g) and N,N-dimethylformamide(35 mL). The reaction flask was heated to 50° C. in an oil bath. The reaction solution was stirred over 20 hours until the reaction was complete. To the reaction solution were added dichloromethane and water to extract. The aqueous phase was back-extracted with dichloromethane twice. The organic phases were combined. The combined organic phase was dried over anhydrous magnesium sulfate, filtered and concentrated under reduced pressure to give a crude product. The crude product was purified with silica gel column chromatography to give the title compound as a yellow solid (2.111 g) (HPLC purity: 96.68%). Yield: 55.3%.

$^1$HNMR (CDCl$_3$, 400 MHz) δ 7.457-7.418(dd, 1H), 7.180-7.161 (dd, 1H), 6.885-6.863 (dd, 1H), 4.966-4.921 (m, 1H), 4.110-3.973 (m, 2H), 2.994-2.926 (m, 1H), 2.820-2.753 (m, 2H), 2.683-2.646 (t, 2H), 2.144 (s, 3H), 2.125-2.079 (m, 1H). MS (m/e): 348.19 (M+H$^+$).

Example 12

Preparation of 4-amino-2-(1-(2-methylsulfinylethyl)-2,6-dioxopiperidin-3-yl)isoindolin-1,3-dione To a reaction flask were added 4-amino-2-(1-(2-methylthioethyl)-2,6-dioxopiperidin-3-yl)-isoindolin-1,3-dione (4.85 g), m-chloroperoxybenzoic acid (3.13 g) and dichloromethane (170 mL). The solution was stirred at the room temperature over 18 hours. To the reaction system was added saturated aqueous solution of sodium bicarbonate (100 mL) to extract. The aqueous phase was back-extracted with dichloromethane (150 mL×3). The organic phases were combined. The combined organic phase was dried over anhydrous magnesium sulfate, filtered and concentrated under reduced pressure to give a crude product. The crude product was purified with silica gel column chromatography to give the title compound 4-amino-2-(1-(2-methylsulfinylethyl)-2,6-dioxopiperidin-3-yl)-isoindolin-1,3-dione (0.846 g) (HPLC purity: 95.09%). Yield: 16.7%.

$^1$HNMR (CDCl$_3$, 400 MHz) δ 7.462-7.423 (dd, 1H), 7.172-7.155 (d, 1H), 6.895-6.874 (d, 1H), 4.974-4.931 (m, 1H), 4.371-4.192 (m, 2H), 3.073-2.909 (m, 3H), 2.827-2.696 (m, 2H), 2.650-2.647 (d, 3H), 2.144-2.104 (m, 1H). MS (m/e): 364.22 (M+H$^+$).

Example 13

Preparation of 4-amino-2-(1-(2-methylsulfonylethyl)-2,6-dioxopiperidin-3-yl)isoindolin-1,3-dione In accordance with the preparation process in Example 12, 4-amino-2-(1-(2-methylthioethyl)-2,6-dioxopiperidin-3- yl)-isoindolin-1,3-dione was used to give the title compound as a yellow solid (1.78 g) (HPLC purity: 99.47%). Yield: 33.6%.

$^1$HNMR (CDCl$_3$, 400 MHz) δ 7.470-7.431 (dd, 1H), 7.184-7.167 (d, 1H), 6.896-6.876 (d, 1H), 4.988-4.943 (m, 1H), 4.400-4.231 (m, 2H), 3.311-3.277 (t, 2H), 2.999 (s, 3H), 3.012-2.932 (m, 1H), 2.834-2.697 (m, 2H), 2.153-2.110 (m, 1H). MS (m/e): 380.23 (M+H$^+$).

Example 14

Preparation of 4-amino-2-(1-(2-methoxyethyl)-3-fluoro-2,6-dioxopiperidin-3-yl)isoindolin-1,3-dione 4-amino-2-(1-(2-methoxyethyl)-2,6-dioxopiperidin-3-yl)-isoindolin-1,3-dione was prepared in accordance with PCT Int. Appl., 2006105697, 12 Oct. 2006.

4-amino-2-(1-(2-methoxyethyl)-2,6-dioxopiperidin-3-yl)-isoindolin-1,3-dione (5 g) was dissolved in tetrahydrofuran (100 mL) under argon atmosphere. The solution was cooled to −78° C. To the solution was slowly added dropwise lithium hexamethyldisilazide (40 mL). After addition, the resultant solution was stirred over 1 hour. To the solution was added N-fluorobenzenesulfonimide (11.67 g in 30 mL of tetrahydrofuran). After addition, the resultant solution was stirred over 1 hour. The resultant solution was slowly heated to the room temperature and reacted overnight. To the reaction mixture were added saturated aqueous solution of ammonium chloride (150 mL) and ethyl acetate (150 mL). The solution was separated. The aqueous phase was extracted with ethyl acetate (100 mL). The organic phases were combined. The combined organic phase was washed with saturated aqueous solution of sodium chloride (200 mL), dried over anhydrous sodium sulfate and filtered. The organic phase was concentrated. The residue was purified with column chromatography (ethyl acetate/petroleum ether=⅓) to give the title compound as a yellow solid (968 mg) (HPLC purity: 97.20%). Yield: 18.4%.

$^1$HNMR (CDCl$_3$, 400 MHz) δ 7.461-7.499 (dd, 1H), 7.171-7.153 (d, 1H), 6.931-6.899 (d, 1H), 4.193-4.024 (m, 2H), 3.670-3.640 (t, 2H), 3.606-3.558 (m, 1H), 3.020 (s, 3H), 2.371-2.960 (m, 1H), 2.656-2.555 (m, 1H), 2.433-2.342 (m, 1H). MS (m/e): 372.22 (M+Na$^+$).

Example 15

Preparation of 4-amino-2-(1-(2-methoxyethyl)-3-methyl-2,6-dioxopiperidin-3-yl)isoindolin-1,3-dione 3-amino-3-methylpiperidin-2,6-dione hydrochloride was prepared in accordance with PCT Int. Appl., 2006081251, Aug. 3, 2006.

Using the preparation process in Example 4, 3-amino-3-methylpiperidin-2,6-dione hydrochloride and 3-nitrophthalic anhydride were reacted to give 2-(3-methyl-2,6-dioxopiperidin-3-yl)-4-nitroisoindolin-1,3-dione as a white solid (2.7 g) (HPLC purity: 66.03%). Yield: 69.1%. MS (m/e): 318.12 (M+H+).

Using the preparation process in Example 11, 2-(3-methyl-2,6-dioxopiperidin-3-yl)-4-nitroisoindolin-1,3-dione was used to prepare 4-nitro-2-(1-(2-methoxyethyl)-3-methyl-2,6-dioxopiperidin-3-yl)-isoindolin-1,3-dione as a yellow solid (0.736 g) (HPLC purity: 96.45%). Yield: 28.3%. MS (m/e): 376.26 (M+H+).

Using the preparation process in Example 7, 4-nitro-2-(1-(2-methoxyethyl)-3-methyl-2,6-dioxopiperidin-3-yl)-isoindolin-1,3-dione was used to give the title compound as yellow solid (0.572 g) (HPLC purity: 94.51%). Yield: 84.1%.

$^1$HNMR (CDCl$_3$, 400 MHz) δ 7.430-7.391 (t, 1H), 7.104-7.086 (d, 1H), 6.854-6.833 (d, 1H), 4.112-4.074 (m, 2H), 3.615-3.580 (m, 2H), 3.373 (s, 3H), 2.844-2.793 (m, 1H), 2.734-2.690 (m, 2H), 2.046-1.993 (m, 1H), 1.969 (s, 3H). MS (m/e): 368.22 (M+Na$^+$).

Example 16

Preparation of 4-acetylamino-2-(1-(3-methoxypropyl)-2,6-dioxopiperidin-3-yl)isoindolin-1,3-dione N-((benzyloxy)carbonyl)-glutamic anhydride was prepared in accordance with Archives of Pharmacal Research, 31(7), 834-837; 2008.

To a reaction flask were added N-((benzyloxy)carbonyl)-glutamic anhydride (19 g), 3-methoxypropylamine (6.4 g), triethylamine (7.3 g), 4-dimethylaminopyridine (0.88 g) and tetrahydrofuran(270 mL). The reaction solution was stirred at the room temperature over 40 hours until the reaction was complete. The resultant reaction was the tetrahydrofuran solution of the product, which was directly used in the next step.

N,N'-carbonyldiiazole (23.4 g) was added into the above reaction solution in batch. The resultant solution was stirred at the room temperature over 72 hours until the reaction was complete. The solution was concentrated under reduced presssure. To the concentrate was added dichloromethane (500 mL). The resultant solution was washed with 1 N hydrochloric acid (250 mL), saturated aqueous solution of sodium bicarbonate (250 mL) and saturated aqueous solution of sodium chloride (250 mL). The organic phase was dried over anhydrous magnesium sulfate, filtered and concentrated under reduced pressure to give 1-(3-methoxypropyl)-3-benzyloxyamido-2,6-piperidinedione as a brown oil (23.7 g), which was directly used in the next step. MS (m/e): 357.24 (M+Na+).

Using the preparation process in Example 4, 1-(3-methoxypropyl)-3-benzyloxyamido-2,6-piperidinedione was used to prepare the title compound as a white solid (0.434 g) (HPLC purity: 97.71%). Yield: 12.5%.

$^1$HNMR (CDCl$_3$, 400 MHz) δ 9.411 (bs, 1H), 8.822-8.801 (d, 1H), 7.729-7.689 (dd, 1H), 7.555-7.535 (dd, 1H), 4.943-4.987 (m, 1H), 3.993-3.879 (m, 2H), 3.428-3.397 (t, 2H), 3.304 (s, 3H), 3.005-2.936 (m, 1H), 2.825-2.705 (m, 2H), 2.266 (s, 3H), 2.146-2.092 (m, 1H), 1.880-1.802 (m, 2H). MS (m/e): 410.31 (M+Na$^+$).

Example 17

Preparation of 4-fluoro-2-(1-(3-methoxypropyl)-2,6-dioxopiperidin-3-yl)isoindolin-1,3-dione Using the preparation process in Example 4, 1-(3-methoxypropyl)-3-amino-2,6-piperidinedione acetate and 3-fluorophthalic anhydride were reacted to give the title compound as a yellowish sticky product (0.631 g) (HPLC purity: 97.42%). Yield: 31.1%.

$^1$HNMR (CDCl$_3$, 400 MHz) δ 7.792-7.743 (m, 1H), 7.715-7.697 (d, 1H), 7.444-7.400 (m, 1H), 4.978-4.932 (m, 1H), 3.988-3.871 (m, 2H), 3.421-3.390 (t, 2H), 3.300 (s, 3H), 3.000-2.938 (m, 1H), 2.851-2.691 (m, 2H), 2.142-2.091 (m, 1H), 1.872-1.797 (m, 2H). MS (m/e): 349.22 (M+H$^+$).

Example 18

Preparation of 5-amino-2-(1-(3-methoxypropyl)-2,6-dioxopiperidin-3-yl)isoindolin-1,3-dione Using the preparation process in Example 4, 5-nitrophthalic anhydride and 1-(3-methoxypropyl)-3-amino-2,6-piperidinedione acetate were reacted to prepare 5-nitro-2-(1-(3-methoxypropyl)-2,6-dioxopiperidin-3-yl)-isoindolin-1,3-dione as a yellowish oily product (1.118 g) (HPLC purity: 98.44%). Yield: 20%. MS (m/e): 376.25 (M+H+).

Using the preparation process in Example 7, 5-nitro-2-(1-(3-methoxypropyl)-2,6-dioxopiperidin-3-yl)-isoindolin-1,3-dione was used to give the title compound as a yellowish solid (0.697 g) (HPLC purity:97.79%). Yield: 67.7%.

$^1$HNMR (CDCl$_3$, 400 MHz) δ 7.624-7.603 (d, 1H), 7.031-7.027 (d, 1H), 6.861-6.835 (dd, 1H), 4.925-4.879 (m, 1H), 3.977-3.863 (m, 2H), 3.421-3.390 (t, 2H), 3.301 (s, 3H), 2.969-2.922 (m, 1H), 2.820-2.676 (m, 2H), 2.108-2.056 (m, 1H), 1.869-1.794 (m, 2H). MS (m/e): 346.24 (M+H$^+$).

Example 19

Preparation of 4-amino-2-(1-(2-ethoxyethyl)-2,6-dioxopiperidin-3-yl)isoindolin-1,3-dione Using the preparation process in Example 16, N-((benzyloxy)carbonyl)-glutamic anhydride was used to prepare 1-(2-ethoxyethyl)-3-benzyloxyamido-2,6-piperidinedione as a brown oily crude product (17.2 g).

Using the preparation process in Example 4, 1-(2-ethoxyethyl)-3-amino-2,6-piperidinedione acetate and 3-nitrophthalic anhydride were reacted to prepare 4-nitro-2-(1-(2-ethoxyethyl)-2,6-dioxopiperidin-3-yl)-isoindolin-1,3-dione as an off-white solid (1.326 g) (HPLC purity: 95.24%). Yield: 39.4%. MS (m/e): 376.23 (M+H$^+$).

Using the preparation process in Example 7, 4-nitro-2-(1-(2-ethoxyethyl)-2,6-dioxopiperidin-3-yl)-isoindolin-1,3-dione was used to prepare 4-amino-2-(1-(2-ethoxyethyl)-2,6-dioxopiperidin-3-yl)-isoindolin-1,3-dione as a yellow solid (0.631 g) (HPLC purity: 94.95%). Yield: 51.7%.

$^1$HNMR (CDCl$_3$, 400 MHz) δ 7.450-7.411 (dd, 1H), 7.174-7.156 (d, 1H), 6.881-6.860 (d, 1H), 4.963-4.918 (m, 1H), 4.119-3.994 (m, 2H), 3.575-3.480 (m, 4H), 3.023-2.921 (m, 1H), 2.839-2.714 (m, 2H), 2.140-2.035 (m, 1H), 1.180-1.145 (t, 3H). MS (m/e): 346.24 (M+H$^+$).

Example 20

Preparation of 4-fluoro-2-(1-(2-ethoxyethyl)-2,6-dioxopiperidin-3-yl)isoindolin-1,3-dione Using the preparation process in Example 4, 1-(2-ethoxyethyl)-3-amino-2.6-piperidinedione acetate and 3-fluorophthalic anhydride were reacted to give the title compound as a yellowish sticky product (1.566 g) (HPLC purity: 98.63%). Yield: 74.7%.

$^1$HNMR (CDCl$_3$, 400 MHz) δ 7.792-7.743 (m, 1H), 7.715-7.698 (d, 1H), 7.444-7.400 (m, 1H), 5.019-4.974 (m, 1H), 4.147-3.984 (m, 2H), 3.570-3.475 (m, 4H), 3.045-2.941 (m, 1H), 2.862-2.733 (m, 2H), 2.167-2.087 (m, 1H), 1.178-1.143 (t, 3H). MS (m/e): 349.23 (M+H$^+$).

Example 21

Preparation of 5-fluoro-2-(1-(2-methoxyethyl)-2,6-dioxopiperidin-3-yl)-isoindolin-1,3-dione Using the preparation process in Example 4, 4-fluorophthalic anhydride and 1-(2-methoxyethyl)-3-amino-2,6-piperidinedione acetate were reacted to give the title compound as a white solid (2.905 g) (HPLC purity: 99.64%). Yield: 77.9%.

$^1$HNMR (CDCl$_3$, 400 MHz) δ 7.912-7.880 (dd, 1H), 7.572-7.549 (dd, 1H), 7.457-7.408 (dt, 1H), 5.023-4.978 (m, 1H), 4.144-3.988 (m, 2H), 3.544-3.512 (m, 2H), 3.342 (s, 3H), 3.056-2.933 (m, 1H), 2.859-2.738 (m, 2H), 2.175-2.080 (m, 1H). MS (m/e): 357.20 (M+Na$^+$).

Example 22

Prepation of 4-amino-2-(1-(4-methodybutyl)-2,6-dioxopiperidin-3-yl)isoindolin-1,3-dione Using the preparation process in Example 11, 3-amino-N-(2,6-dioxo-3-piperidinyl)-phthalimide and 1-bromo-4-methoxybutane were reacted to give the title compound as a yellow solid(2.625 g) (HPLC purity: 99.02%). Yield: 79.9%.

$^1$HNMR (CDCl$_3$, 400 MHz) δ 7.455-7.416 (dd, 1H), 7.178-7.160 (dd, 1H), 6.884-6.863 (dd, 1H), 4.927-4.882 (m, 1H), 3.858-3.816 (m, 2H), 3.402-3.371 (t, 2H), 3.317 (s, 3H), 3.007-2.916(m, 1H), 2.819-2.685 (m, 2H), 2.117-2.067 (m, 1H), 1.651-1.571 (m, 4H). MS (m/e): 360.28 (M+H±).

Example 23

Preparation of 4-hydroxy-2-(1-(2-methoxyethyl)-2,6-dioxopiperidin-3-yl)isoindolin-1,3-dione Using the preparation process in Example 4, 3-hydroxyphthalic anhydride and 1-(2-methoxyethyl)-3-amino-2,6-piperidinedione acetate were reacted to give the title compound as a white solid (2.833 g) (HPLC purity: 99.54%). Yield: 80.1%.

$^1$HNMR (CDCl$_3$, 400 MHz) δ 7.649-7.609 (dd, 1H), 7.539 (bs, 1H), 7.430-7.412 (d, 1H), 7.214-7.193 (d, 1H), 4.980-4.934 (m, 1H), 4.146-3.991 (m, 2H), 3.549-3.516 (m, 2H), 3.342 (s, 3H), 3.048-2.941 (m, 1H), 2.843-2.724 (m, 2H), 2.165-2.083 (m, 1H). MS (m/e): 333.19 (M+H$^+$).

Example 24

Preparation of 4-methyl-2-(1-(2-methoxyethyl)-2,6-dioxopiperidin-3-yl)-isoindolin-1,3-dione Using the preparation process in Example 4, 3-methylphthalic anhydride and 1-(2-methoxyethyl)-3-amino-2,6-piperidinedione acetate were reacted to give the title compound as a white solid (2.348 g) (HPLC purity: 98.36%). Yield: 68.1%.

$^1$HNMR (CDCl$_3$, 400 MHz) δ 7.716-7.697 (d, 1H), 7.623-7.586 (t, 1H), 7.508-7.489 (d, 1H), 5.017-4.972 (m, 1H), 4.143-3.996 (m, 2H), 3.547-3.516 (t, 2H), 3.344 (s, 3H), 3.006-2.944 (m, 1H), 2.855-2.732 (m, 2H), 2.698 (s, 3H), 2.153-2.084 (m, 1H). MS (m/e): 353.23 (M+Na$^+$).

Example 25

Preparation of 4-amino-5-methoxy-2-(1-(2-methoxyethyl)-2,6-dioxopiperidin-3-yl)-isoindolin-1,3-dione To a reaction flask were added 4-amino-5-hydroxy-2-(1-(2-methoxyethyl)-2,6-dioxopiperidin-3-yl)-isoindolin-1,3-dione (2.5 g), methyl iodide (1.02 g), potassium carbonate (1.99 g) and N,N-dimethylformamide (25 mL). The solution was stirred at the room temperature over 16 hours until the reaction was complete. The solution was added into water at the room temperature. The resultant solution was stirred and filtered. The filter cake was collected as crude product. The crude product was dissolved and purified with methyl tert-butyl ether/ethyl acetate to give the title compound as a yellow solid (1.94 g) (HPLC purity: 96.08%). Yield: 74.6%.

$^1$HNMR (CDCl$_3$, 400 MHz) δ 7.180-7.160 (d, 1H), 6.891-6.871 (d, 1H), 5.388 (bs, 2H), 4.954-4.909 (m, 1H), 4.136-3.987 (m, 2H), 3.943 (s, 3H), 3.541-3.511 (t, 2H), 3.340 (s, 3H), 2.983-2.944 (m, 1H), 2.793-2.744 (m, 2H), 2.130-2.035 (m, 1H). MS (m/e): 362.22 (M+H$^+$).

Example 26

Preparation of 4-amino-2-(1-(3-methoxypropyl)-2,6-dioxopiperidin-3-yl)isoindolin-1,3-dione To a three-neck flask (100 mL) were added 3-nitrophthalic anhydride (5 g, 25.9 mmol), L-glutamine (3.782 g, 25.9 mmol), and acetonitrile (45 mL). The reaction solution was magnetically stirred under argon atmosphere. The reaction solution was refluxed at 90° C. over 14 hours. After the reaction was complete, the solution was cooled. To the solution was added N,N'-carbonyldiiazole (12.591 g, 77.7 mmol) at the room temperature. The solution was stirred at the room temperature until no bubble was released. The resultant solution was reacted over 1 hour in an oil bath of 84° C. The solution was cooled to the room temperature. The solution was added into hydrochloric acid (225 mL, 1 mol/L) with vigorously stirring. The resultant solution was stirred and filtered. The filter cake was dissolved in absolute ethanol (25 mL). The solution was filtered. The resultant solid was dried in vacuo to give 2-(2,6-dioxopiperidin-3-yl)-4-nitroisoindolin-1,3-dione (5.125 g) as a yellow product. Yield: 65.3%.

To a single-neck flask (100 mL) were added 2-(2,6-dioxopiperidin-3-yl)-4-nitroisoindolin-1,3-dione (3 g, 9.9 mmol) and N,N-dimethylformamide (45 mL). Sodium hydride (content: 60%, 0.872 g, 21.8 mmol) was added in one portion. The solution was stirred at the room temperature over 15 minutes. To the solution was slowly added dropwise 3-bromopropyl methyl ether (1.8 g, 12 mmol) in N,N-dimethylformamide (4 mL). After addition, the reaction continued over 2.5 hours. The reaction solution was poured into saturated aqueous solution of ammonium chloride (400 mL). The resultant solution was extracted with ethyl acetate (200 mL×3). The organic phases were combined. The combined organic phase was dried over anhydrous sodium sulfate and filtered. The filtrate was concentrated. The residue was separated with column chromatography to give 4-nitro-2-(1-(3-methoxypropyl)-2,6-dioxopiperidin-3-yl)isoindolin-1,3-dione (1.211 g). Yield: 32.3%.

To a single-neck flask were added 4-nitro-2-(1-(3-methoxypropyl)-2,6-dioxopiperidin-3-yl)isoindolin-1,3-dione (1.875 g, 5 mmol), palladium on carbon (10%, 0.4 g), methanol (10 mL), tetrahydrofuran (10 mL). The air was replaced with hydrogen. The solution was stirred at the room temperature and under atmospheric pressure overnight. After the reaction was complete, the solution was filtered with diatomite. The filtrate was concentrated. The residue was separated with column chromatography to give the title compound 4-amino-2-(1-(3-methoxypropyl)-2,6-dioxopiperidin-3-yl)isoindolin-1,3-dione (1.135 g). HPLC purity: 96.51%. Yield: 65.8%.

MS(m/e): 346 (M+H$^+$)

Example 27

Preparation of 4-amino-2-(1-(2-methoxyethyl)-2,6-dioxopiperidin-3-yl)isoindolin-1,3-dione The Chinese patent No. ZL200510013292.3 discloses the preparation process of 4-amino-2-(1-(2-methoxyethyl)-2,6-dioxopiperidin-3-yl)isoindolin-1,3-dione, which is incorporated herein by reference in its entirety.

Alternatively, in accordance with the preparation process in Example 27, 3-bromopropyl methyl ether was replaced with 3-bromoethyl methyl ether to prepare the title compound.

$^1$HNMR (CDCl$_3$, 600 MHz) δ 7.38 (t, 1H), 7.11 (d, 1H), 6.85 (d, 1H), 5.30 (bs, 2H), 4.95-4.98 (m, 1H), 4.09-4.13 (m, 1H), 4.00-4.04 (m, 1H), 3.52-3.54 (m, 2H), 3.34(s, 3H), 2.96-2.99 (m, 1H), 2.76-2.75 (m, 1H), 2.78-2.80 (m, 1H), 2.08-2.11 (m, 1H). MS (m/e): 332 (M+H$^+$).

Biological Example 1

Effects of piperidine-2,6-dione Derivatives on Treatment of DSS-Induced Inflammatory Bowel Disease Models in Mice 1.1 Experimental Materials Experimental animals: C57BL/6J mice, weight of 16-18 g 5-ASA, cyclosporine A, DSS, sodium carboxymethyl cellulose Piperidine-2,6-dione derivatives, 5-ASA or Cyclosporine A: Preparation Method: Suspended with 1% CMC-Na, and prepared when it was needed.

1.2 Experimental Method

54 C57BL/6 mice were randomly divided into 6 groups: normal control group, model control group, Example 27 groups consisting of dose of 5 mg/Kg group, dose of 10 mg/Kg group and dose of 20 mg/Kg group, and cyclosporine A-25 mg/Kg group. There were 9 mice in each group (see Table 2 below). Besides the normal control group, the remaining groups were induced with 1.6% DSS for 8 days. Normal drinking water was then administered for 3 days. The normal control group was administered with normal drinking water all the time. The model control group and the compound in Example 27 group were administered with 1% CMC-Na or the corresponding drug every day until the end of the experiment. The cyclosporine A group was administered with the corresponding drug every day from the first day of experiment to the eighth day of the experiment and was administered with the corresponding volume of 1% CMC-Na every day from the ninth day to the end of the experiment due to toxicity. At the end of the experiment, the animals were treated and the indexes such as the colon length were tested.

TABLE 2

Grouped Table

| Groups | Administration Route | DSS Concentration (%) | Daily Administration Dose (mg/Kg/d) | Administration Frequency | Administration Volume (mL/Kg) | Number of Animals |
|---|---|---|---|---|---|---|
| Normal Control Group | i.g | 0 | 0 | Q.D | 10 | 9 |
| Model Control Group | i.g | 1.6 | 0 | Q.D | 10 | 9 |
| Example 27 Group | i.g | 1.6 | 5 | Q.D | 10 | 9 |
| Example 27 Group | i.g | 1.6 | 10 | Q.D | 10 | 9 |
| Example 27 Group | i.g | 1.6 | 20 | Q.D | 10 | 9 |
| Cyclosporine A | i.g | 1.6 | 25 | Q.D | 10 | 9 |

Note:
i.g: intragastric administration;
Q.D: once per day 1.3 Data Processing Method and Statistical Method:

The homogeneity of data variance test was performed by Spss13.0. Where the variance of data was homogeneous ($P>0.05$), one-way ANOVA LSD test was performed. Where the variance was inhomogeneous ($P≤0.05$), the data were treated with extraction of a root and homogeneity of data variance test was further performed. Where the variance of data was homogeneous ($P>0.05$), one-way ANOVA LSD test was performed. Where the variance was still inhomogeneous ($P≤0.05$), then Dunnett's multiple comparison (parameter method) was performed.

1.4 Experimental Results:

After the eighth day of the experiment, the body weights of the animals in the model control group showed a decline trend, while faeces of half of the aminals are abnormal such as loose stool, bloody stool and the like. During the experiment, the body weight of the animals in 20 mg/Kg groups of Example 27 had a continuous increase trend, which is equivalent to the normal control group. It was demonstrated that 20 mg/Kg groups of Example 27 can significantly improve the decrease of the body weights of the model animals and have better protective effects on the model animals, which indicated the therapeutical effects on the model animals. The body weights of the animals in the cyclosporine A group were generally lower than those in the normal control group.

Disease Activity Index (DAI): During the experiment, the DAI of the dose of 20 mg/Kg group of Example 27 is equivalent to the DAI of the normal control group and cyclosporine A group. The DAIs of the dose of 5 mg/Kg, 10 mg/Kg, and 20 mg/Kg groups of Example 27 are better than the DAI of model control group.

At the end of the experiment, the results of the colon length showed a significant reduction in colon length in the model control group (5.9±0.2 cm, P<0.05) compared with the normal control group. The reduction in colon length was relieved in cyclosporine A group and each dose group of Example 27. In particular, the reduction in colon length was significantly relieved in the dose of 20 mg/Kg group of Example 27 (6.4±0.4 cm, P<0.05) and cyclosporine A group with the dose of 25 mg/Kg (6.4±0.5 cm, P<0.05), which demonstrated that the compound of Example 27 and cyclosporine A had better effects on the model.

The compound of Example 27 had better dosage effects on relief of reduction in colon length in the model. The compound of Example 27 at the dose of 5 mg/Kg had certain relief effects in the model, while the compound of Example 27 at the dose of 20 mg/Kg had significant relief effects in the model. Therefore, the compound of Example 27 had better relief effects in the model.

TABLE 3

The mean values of colon length in each test group (Unit: cm)

| Groups | Mean ± SD |
|---|---|
| Normal Control Group | 6.6 ± 0.7 |
| Model Control Group | 5.9 ± 0.2* |
| Cyclosporine A Group-25 mg/Kg | 6.4 ± 0.5# |
| Compound in Example 27 Group-5 mg/Kg | 6.1 ± 0.4 |
| Compound in Example 27 Group-10 mg/Kg | 6.2 ± 0.4 |
| Compound in Example 27 Group-20 mg/Kg | 6.4 ± 0.4# |

Note:
*compared with the normal control group, P < 0.05.
compared with the model control group, P < 0.05.
Mean ± SD: average value ± standard deviation.

Biological Example 2

Effects of piperidine-2,6-dione Derivatives on Treatment of DSS-Induced Inflammatory Bowel Disease Models in Mice 2.1 Experimental Materials The experimental materials used in the present biological example are identical to those in Biological Example 1.

2.2 Experimental Method 66 female C57BL/6 mice were randomly divided into 6 groups: normal control group, model control group, cyclosporine A (25 mg/Kg), 5-ASA (100 mg/Kg), the compound in Example 27 (30 mg/Kg) and the compound in Example 26 (30 mg/Kg). There were 11 mice in each group (see Table 4 below). Besides the normal control group, the remaining groups were induced with 0.9% DSS for 5 days. The day of induction was the first day of the test and then normal drinking water was administered for 4 days. The normal control group was administered with normal drinking water all the time. The model control group, 5-ASA group, the compound in Example 27 group and the compound in Example 26 group were administered with 1% CMC-Na or the corresponding drug every day from the first day of the experiment to the end of the experiment. The cyclosporine A group was administered with cyclosporine A every day from the first day of experiment to the fifth day of the experiment and was administered with the corresponding volume of 1% CMC-Na every day from the sixth day to the end of the experiment due to toxicity. The normal control group was administered with the corresponding volume of 1% CMC-Na every day. The animals were treated and the indexes were tested at the end of the experiment.

The compound in Example 27, the compound in Example 26, 5-ASA or Cyclosporine A: Preparation Method: Suspended with 1% CMC-Na, and prepared when it was needed.

TABLE 4

Grouped Table

| Groups | Administration Route | DSS concentration (%) | Daily Administration Dose (mg/Kg/d) | Administration Frequency | Numbers of animals | Solvent |
|---|---|---|---|---|---|---|
| Normal Control Group | i.g | 0.0 | 0 | Q.D | 11 | 1% CMC-Na |
| Model Control Group | i.g | 0.9 | 0 | Q.D | 11 | 1% CMC-Na |
| 5-ASA Group | i.g | 0.9 | 100 | Q.D | 11 | 1% CMC-Na |
| Cyclosporine A Group | i.g | 0.9 | 25 | Q.D | 11 | 1% CMC-Na |
| Example 27 Group | i.g | 0.9 | 30 | Q.D | 11 | 1% CMC-Na |
| Example 26 Group | i.g | 0.9 | 30 | Q.D | 11 | 1% CMC-Na |

Note:
i.g: intragastric administration;
Q.D: once per day;
mg/kg/d: milligrams/kilogram/day 2.3 Data Processing Method and Statistical Method: One-Way Anova Test was Performed With SPSS 17.0. The Colony Length was Analyzed Statistically Between Groups.

2.4 Experimental Results:

TABLE 5

The mean values of colon length in each test group (Unit: cm)

| Groups | Mean ± SD |
|---|---|
| Normal Control Group | 6.6 ± 0.4 |
| Model Control Group | 5.9 ± 0.4** |
| 5-ASA Group-100 mg/Kg | 6.1 ± 0.4 |
| Cyclosporine A Group-25 mg/Kg | 6.2 ± 0.5 |
| Compound in Example 27 Group-30 mg/Kg | 6.3 ± 0.5 |
| Compound in Example 26 Group-30 mg/Kg | 6.3 ± 0.5 |

Note:
**compared with the normal control group, $P < 0.01$.

At the end of the experiment, the average body weight of each treatment group was higher than that of the model control group. During the whole experiment, the body weights of cyclosporine A group, the compound in Example 27 group and the compound in Example 26 group were higher than that of the model control group. Therefore, it was demonstrated that cyclosporine A group, the compound in Example 27 group and the compound in Example 26 group can improve the decrease of the body weights of model animals and protect the model animals.

At the end of the experiment, the results of the colon length showed a significant reduction in colon length in the model control group compared with the normal control group. Compared with the model control group, each of the treatment group relieved the colonic reduction, wherein cyclosporine A group (P=0.12), the compound in Example 27 group (P=0.07) and the compound in Example 26 group (P=0.06) alleviated the colonic reduction by more than 40%, showing a good improvement on colon injury in the model animals.

In view of the above, in the present experiment, the compound in Example 27 and the compound in Example 26 can reduce the degree of weight loss of model animals and alleviate the colonic reduction, which has better effects on prevention and treatment for the model animals.

Biological Example 3

Effects of piperidine-2,6-dione Derivatives on Treatment of DSS-Induced Inflammatory Bowel Disease Models in Mice 3.1 Experimental Materials The experimental materials used in the present biological example are identical to those in Biological Example 1.

3.2 Experimental Method 40 healthy female C57BL/6 mice having weight of 16-19 g were randomly divided into 4 groups in accordance with weight. There were 10 mice in each group (see Table 6 below). The first day of the experiment was recorded as Day 0. The administration regimen and induction regimen were detailed in Table 6. The change in weight of experimental animals was recorded every day. The experiment was terminated two to three days after the weight of animals in the model group significantly reduced. Samples of animal colonic tissues were obtained to measure the length. One-way ANOVA analysis of mice weights was performed by SPSS22. Statistical analyses between groups were performed. Mann-Whitney U non-parametric test was performed on the length of colon.

TABLE 6

Grouped Table

| Groups | DSS Concentration (%) | Administration Rout | Dose (mg/Kg) | Administration Frequency | Solvent | Number of Animals |
|---|---|---|---|---|---|---|
| Blank Control Group | — | — | — | — | — | 10 |
| Model Control Group | 1.0 | i.g | — | Q.D | 1% CMC-Na | |
| Example 7 | | | 30 | | | |
| Example 4 | | | | | | |

TABLE 7

| Induction Concentration of Daily Actual DSS-induced Drinking (%) | | | | | | | | | | | | | | |
|---|---|---|---|---|---|---|---|---|---|---|---|---|---|---|
| Day | 0 | 1 | 2 | 3 | 4 | 5 | 6 | 7 | 8 | 9 | 10 | 11 | 12 | 13 |
| DSS Concentration (%) | 1.0 | 1.0 | 1.0 | 1.0 | 1.0 | 1.5 | 1.5 | 1.5 | 1.5 | 1.5 | 0 | 0 | 0 | 0 |

3.3 Experimental Results

TABLE 8

Table of Body Weights of Experimental Mice over 13 Days (g, Mean ± SD)

| | Blank Control Group | Model Control Group | Example 7 Group | Example 4 Group |
|---|---|---|---|---|
| Day 0 | 17.7 ± 1.0 | 17.4 ± 0.8 | 17.4 ± 0.8 | 17.4 ± 1.3 |
| Day 1 | 17.4 ± 0.9 | 17.5 ± 0.7 | 17.5 ± 0.7 | 17.6 ± 1.1 |
| Day 2 | 17.7 ± 0.9 | 18.0 ± 0.8 | 18.2 ± 0.8 | 18.0 ± 0.9 |
| Day 3 | 17.8 ± 0.9 | 17.8 ± 0.8 | 17.8 ± 0.8 | 17.8 ± 1.0 |
| Day 4 | 18.0 ± 0.9 | 17.9 ± 0.8 | 17.7 ± 0.7 | 17.9 ± 0.9 |
| Day 5 | 18.1 ± 0.8 | 17.9 ± 0.8 | 17.9 ± 0.8 | 18.1 ± 1.1 |
| Day 6 | 17.8 ± 0.9 | 17.5 ± 0.8 | 17.8 ± 0.8 | 17.7 ± 0.9 |
| Day 7 | 18.4 ± 0.8 | 17.7 ± 0.7 | 17.9 ± 0.8 | 18.1 ± 0.9 |
| Day 8 | 18.3 ± 1.0 | 17.1 ± 0.7 | 17.4 ± 0.7 | 17.8 ± 0.8 |
| Day 9 | 18.7 ± 1.0 | 16.8 ± 0.8 | 17.4 ± 0.7 | 17.6 ± 0.8 |
| Day 10 | 18.4 ± 1.0 | 16.0 ± 0.8 | 16.8 ± 0.9 | 17.0 ± 0.7 |
| Day 11 | 18.8 ± 1.0 | 15.7 ± 0.8 | 16.8 ± 1.0 | 16.7 ± 0.7 |
| Day 12 | 18.8 ± 0.9 | 15.8 ± 0.8 | 17.3 ± 1.0 | 17.0 ± 0.9 |

TABLE 9

Average Length of Colon (cm, Mean ± SD) and Inhibitory Rate of Colonic Reduction (%) in Each Group of Experimental Animals

| | Blank Control Group | Model Control Group | Example 7 Group | Example 4 Group |
|---|---|---|---|---|
| Length (cm) | 6.8 ± 0.4 | 5.7 ± 0.3*** | 6.4 ± 0.4## | 6.3 ± 0.3## |
| Inhibitory Rate of Colonic Reduction (%) | | | 63.6 | 54.5 |

Note:
***compared with the blank control group, P < 0.001;
compared with the model control group, 0.001 ≤ P < 0.01.

Calculation Formula of Inhibitory Rate of Colonic Reduction: (Length of Colon in Administration Group−Length of Colon in Model Group)/ (Length of Colon in Blank Group−Length of Colon in Model Group)

At the end of the experiment, the average body weight of each treatment group was higher than that of the model control group. During the whole experiment, the body weights of the compound in Example 7 group and the compound in Example 4 group were higher than that of the model control group. Therefore, it was demonstrated that the compound in Example 7 group and the compound in Example 4 can improve the decrease of the body weights of model animals and protect the model animals.

At the end of the experiment, the results of the colon length showed a significant reduction in colon length in the model control group compared with the normal control group. Compared with the model control group, each of the treatment group relieved the colonic reduction.

Biological Example 4

Effects of piperidine-2,6-dione Derivatives on Treatment of DSS-Induced Inflammatory Bowel Disease Models in Mice 4.1 Experimental Materials The experimental materials used in the present biological example are identical to those in Biological Example 1.

4.2 Experimental Method

The experimental method used in the present biological example is identical to those in Biological Example 3.

TABLE 10

Grouped Table

| Groups | DSS Concentration (%) | Administration Rout | Dose (mg/Kg) | Administration Frequency | Solvent | Number of Animals |
|---|---|---|---|---|---|---|
| Blank Control Group | — | — | — | — | — | 10 |
| Model Control Group | 1.3 | i.g | — | Q.D | 1% CMC-Na | |
| Example 2 | | | 30 | | | |
| Example 19 | | | | | | |
| Example 16 | | | | | | |
| Example 6 | | | | | | |

TABLE 11

Induction Concentration of Daily Actual DSS-induced Drinking (%)

| | 0 | 1 | 2 | 3 | 4 | 5 | 6 | 7 | 8 | 9 |
|---|---|---|---|---|---|---|---|---|---|---|
| DSS Concentration (%) | 1.3 | 1.3 | 1.3 | 1.3 | 1.3 | 1.3 | 0 | 0 | 0 | 0 |

4.3 Experimental Results

TABLE 12

Table of Weights of Experimental Mice over 9 Days (g, Mean ± SD)

| | Blank Control Group | Model Control Group | Example 2 Group | Example 19 Group | Example 16 Group | Example 6 Group |
|---|---|---|---|---|---|---|
| Day 0 | 19.7 ± 0.9 | 19.7 ± 1.0 | 20.1 ± 0.8 | 19.6 ± 0.7 | 19.8 ± 0.6 | 19.8 ± 0.6 |
| Day 1 | 19.5 ± 0.8 | 19.8 ± 0.8 | 20.0 ± 0.7 | 19.6 ± 0.8 | 19.9 ± 0.4 | 19.9 ± 0.7 |
| Day 2 | 19.4 ± 0.6 | 19.7 ± 0.6 | 19.8 ± 0.6 | 19.7 ± 0.7 | 19.7 ± 0.4 | 19.7 ± 0.7 |
| Day 3 | 19.9 ± 0.6 | 20.0 ± 0.7 | 20.2 ± 0.8 | 19.9 ± 0.7 | 19.9 ± 0.6 | 20.0 ± 0.6 |
| Day 4 | 19.8 ± 0.7 | 20.0 ± 0.7 | 20.2 ± 0.8 | 20.0 ± 0.7 | 19.7 ± 0.5 | 20.0 ± 0.6 |
| Day 5 | 19.8 ± 0.7 | 19.6 ± 0.9 | 20.0 ± 0.6 | 19.7 ± 0.5 | 19.6 ± 0.5 | 19.9 ± 0.7 |
| Day 6 | 19.8 ± 0.8 | 18.7 ± 1.1 | 18.9 ± 0.6 | 19.2 ± 0.7 | 19.3 ± 0.7 | 19.5 ± 0.6 |
| Day 7 | 20.0 ± 0.7 | 18.6 ± 1.0 | 18.8 ± 0.7 | 18.9 ± 0.8 | 19.0 ± 1.0 | 19.4 ± 0.8 |
| Day 8 | 19.9 ± 0.6 | 17.8 ± 1.5 | 18.8 ± 1.0 | 19.0 ± 1.0 | 18.9 ± 1.2 | 19.5 ± 0.7 |
| Day 9 | 20.2 ± 0.5 | 18.1 ± 1.5 | 19.0 ± 1.1 | 19.4 ± 0.8 | 18.9 ± 1.1 | 19.6 ± 1.1 |

TABLE 13

Average Length of Colon (cm, Mean ± SD) in Each Group of Experimental Animals

|  | Blank Control Group | Model Control Group | Example 2 Group | Example 19 Group | Example 16 Group | Example 6 Group |
|---|---|---|---|---|---|---|
| Length | 7.4 ± 0.6 | 5.9 ± 0.7** | 6.9 ± 0.2# | 6.9 ± 0.4# | 7.0 ± 0.4# | 6.9 ± 0.3# |
| Inhibitory Rate of Colonic Reduction (%) |  |  | 66.7 | 66.7 | 73.3 | 66.7 |

Note:
As the variance of overall data of body weights per length was inhomogeneous, Dunnett's T3 analysis was used in one-way ANOVA.
**compared with the blank control group, $0.001 \leq P < 0.01$;
compared with the model control group, $P < 0.05$.

Calculation Formula of Inhibitory Rate of Colonic Reduction: (Length of Colon in Administration Group—Length of Colon in Model Group)/(Length of Colon in Blank Group–Length of Colon in Model Group)

At the end of the experiment, the average body weight of each treatment group was higher than that of the model control group. During the whole experiment, the treatment groups can improve the decrease of the body weights of model animals and protect the model animals.

At the end of the experiment, the results of the colon length showed a significant reduction in colon length in the model control group compared with the normal control group. Compared with the model control group, each of the treatment group relieved the colonic reduction.

Biological Example 5

Effects of piperidine-2,6-dione Derivatives on Treatment of DSS-Induced Inflammatory Bowel Disease Models in Mice 5.1 Experimental Materials The experimental materials used in the present biological example are identical to those in Biological Example 1.

5.2 Experimental Method

The experimental method used in the present biological example is identical to those in Biological Example 3.

TABLE 15

Induction Concentration of Daily Actual DSS-induced Drinking (%)

|  | 0 | 1 | 2 | 3 | 4 | 5 | 6 | 7 | 8 |
|---|---|---|---|---|---|---|---|---|---|
| DSS Concentration (%) | 1.3 | 1.3 | 1.3 | 1.3 | 1.3 | 1.3 | 0 | 0 | 0 |

One-way ANOVA analysis of mice body weights and colonic weights per length was performed by SPSS22. Statistical analyses between groups were performed.

5.3 Experimental Results

TABLE 16

Average Length of Colon (cm, Mean ± SD) and Inhibitory Rate of Colonic Reduction (%) in Each Group of Experimental Animals

| Groups | Length (cm, Mean ± SD) | Inhibitory Rate of Colonic Reduction (%) |
|---|---|---|
| Blank Control Group | 6.9 ± 0.2 |  |
| Model Control Group | 5.8 ± 0.2*** |  |
| Example 27 | 6.7 ± 0.4## | 81.8 |
| Example 21 | 6.9 ± 0.4### | 100.0 |
| Example 15 | 6.6 ± 0.4# | 72.7 |
| Example 24 | 6.7 ± 0.6# | 81.8 |
| Example 23 | 6.9 ± 0.5## | 100.0 |
| Example 22 | 6.9 ± 0.4### | 100.0 |

TABLE 14

Grouped Table

| Groups | DSS Concentration (%) | Administration Rout | Dose (mg/Kg) | Administration Frequency | Solvent | Number of Animals |
|---|---|---|---|---|---|---|
| Blank Control Group | — | — | — | — | — | 10 |
| Model Control Group | 1.3 | i.g | — | Q.D | 1% CMC-Na |  |
| Example 27 |  |  | 30 |  |  |  |
| Example 21 |  |  |  |  |  |  |
| Example 15 |  |  |  |  |  |  |
| Example 24 |  |  |  |  |  |  |
| Example 23 |  |  |  |  |  |  |
| Example 22 |  |  |  |  |  |  |
| Example 13 |  |  |  |  |  |  |
| Example 12 |  |  |  |  |  |  |
| Example 17 |  |  |  |  |  |  |
| Example 20 |  |  |  |  |  |  |
| Example 25 |  |  |  |  |  |  |

TABLE 16-continued

Average Length of Colon (cm, Mean ± SD) and Inhibitory Rate of Colonic Reduction (%) in Each Group of Experimental Animals

| Groups | Length (cm, Mean ± SD) | Inhibitory Rate of Colonic Reduction (%) |
|---|---|---|
| Example 13 | 6.9 ± 0.4## | 100.0 |
| Example 12 | 7.0 ± 0.5## | 109.1 |
| Example 17 | 7.0 ± 0.4### | 109.1 |
| Example 20 | 6.9 ± 0.6# | 100.0 |
| Example 25 | 6.7 ± 0.5# | 81.8 |

Note:
***compared with the blank control group, P < 0.001;
compared with the model control group, P < 0.05;
compared with the model control group, 0.001 ≤ P < 0.01;
compared with the model control group, P < 0.001.

Calculation Formula of Inhibitory Rate of Colonic Reduction: (Length of Colon in Administration Group−Length of Colon in Model Group)/(Length of Colon in Blank Group−Length of Colon in Model Group)

At the end of the experiment, the average body weight of each treatment group was higher than that of the model control group. During the whole experiment, the treatment groups can improve the decrease of the body weight of model animals and protect the model animals.

At the end of the experiment, the results of the colon length showed a significant reduction in colon length in the model control group compared with the normal control group. Compared with the model control group, each of the treatment group relieved the colonic reduction.

Biological Example 6

Acute Toxicity Experiment of Single Oral Administration of Piperidine-2,6-dione Derivatives in Mice Experimental Process The mice were fasted one day before the experiment. On the day of the experiment, 6 mice (ICR mice, body weight of 19-21 g, three females and three males) were selected in each experiment group. First of all, one female and one male were selected to orally give 1000 mg/Kg, and observed for 5-10 minutes. If there were no obvious side effects, the remaining 4 animals were orally given the same dose, and observed for 10-15 minutes. If no animal died, the animals were placed in a box to balancedly feed for 7 days. The state was observed and the body weight was recorded daily. The animal grouping plan and the initial dose of the drug were shown in the table below:

TABLE 17

Information Table of Animal Groups

| Schedule | Groups | Administration Dose mg/Kg | Administration Volume ml/Kg | Drug Concentration mg/mL | Solvent | Number of Animals |
|---|---|---|---|---|---|---|
| Day 1 | Blank Control | — | 15 | — | 1% CMC-Na | Three females and three males |
| | Example 1 | 1000 | | 66.67 | | |
| | Example 8 | | | | | |
| | Example 3 | | | | | |
| | Example 2 | | | | | |
| | Example 4 | | | | | |
| | Example 24 | | | | | |
| Day 2 | Example 23 | | | | | |
| | Example 10 | | | | | |
| | Example 2 | | | | | |
| | Example 11 | | | | | |
| | Example 20 | | | | | |
| | Example 17 | | | | | |
| | Example 13 | | | | | |
| | Example 12 | | | | | |
| Day 3 | Example 19 | | | | | |
| | Example 26 | | | | | |
| | Example 6 | | | | | |
| | Example 3 | | | | | |
| | Example 9 | | | | | |

Observation Indexes Within 0-15 Minutes After Administration
  Activity: restlessness, hyperactivity
  Nervous system response: tremor, spasm, convulsion, ataxia, posture abnormality, etc.
  Autonomic nerve: exophthalmos, salivation, tears, urination (hematuria), diarrhea, piloerection, breathing, etc.
Observation Indexes Over 7 Days
  Body weight
  State of Animal: lethargy, hyperactivity, excitement, hair loss, diarrhea, abnormal behavior, death, etc.

Experimental Results

TABLE 18

Summary Table of Toxic Response of Tested Animals in 7 Days

| Group | Sex | Summary of toxic response of tested animals in 7 Days |
|---|---|---|
| Example 23 | Male | Abnormality was not observed in 7 days of the test |
|  | Female | Abnormality was not observed in 7 days of the test |
| Example 10 | Male | Decrease of activity was observed in all the animals within 30 minutes after administration but activity was recovered within this period. Abnormality was not observed in all the animals from day 2 to 7. |
|  | Female | Decrease of activity was observed in all the animals within 30 minutes after administration but activity was recovered within this period. Abnormality was not observed in all the animals from day 2 to 7. |
| Example 2 | Male | Slight abnormality of activity was occasionally observed in two animals but activity was recovered within in 30 minutes. Abnormality was not observed in all the animals from day 2 to 7. |
|  | Female | Abnormality was not observed in 7 days of the test |
| Example 11 | Male | Abnormality was not observed in 7 days of the test |
|  | Female | Decrease of activity was observed in one animal after administration but activity was recovered within 3 minutes. Abnormality was not observed in all the animals from day 2 to 7. |
| Example 20 | Male | Decrease of activity was observed in one animal 11 minutes after administration but activity was recovered later. Abnormality was not observed in all the animals from day 2 to 7. |
|  | Female | Decrease of activity was observed in two animals in 10 minutes after administration but activity was recovered later. Abnormality was not observed in all the animals from day 2 to 7. |
| Example 17 | Male | Motor dysfunction in two animals was observed 30 minutes after administration and function was recovered later. Abnormality was not observed in all the animals from day 2 to 7. |
|  | Female | Motor dysfunction in one animal was observed 10 minutes after administration and function was recovered later. Abnormality was not observed in all the animals from day 2 to 7. |
| Example 13 | Male | Abnormality was not observed in 7 days of the test |
|  | Female | Abnormality was not observed in 7 days of the test |
| Example 12 | Male | Abnormality was not observed in 7 days of the test |
|  | Female | Abnormality was not observed in 7 days of the test |
| Example 19 | Male | Severe motor dysfunction in two animals was observed 30 minutes after administration and function was recovered in about 2 hours. Abnormality was not observed in all the animals from day 2 to 7. |
|  | Female | Severe motor dysfunction in three animals was observed 30 minutes after administration and function was recovered in about 2 hours. Abnormality was not observed in all the animals from day 2 to 7. |
| Example 26 | Male | Abnormality was not observed in 7 days of the test |
|  | Female | Abnormality was not observed in 7 days of the test |
| Example 6 | Male | Abnormality was not observed in 7 days of the test |
|  | Female | Abnormality was not observed in 7 days of the test |
| Example 3 | Male | Abnormality was not observed in 7 days of the test |
|  | Female | Abnormality was not observed in 7 days of the test |
| Example 9 | Male | Abnormality was not observed in 7 days of the test |
|  | Female | Abnormality was not observed in 7 days of the test |

Note:
The dosage is 1000 mg/Kg in Table 18 unless indicated otherwise.
"n = 1" indicate the number of the tested animal in the group is one. The number of the tested animal is 3 where "n = 1" is not indicated in the group.
Abnormality is not observed where the observation index is not mentioned.

TABLE 19

Table of Daily Body Weight of Tested Male Mice (g, Mean ± SD)

|  | Day 1 | Day 2 | Day 3 | Day 4 | Day 5 | Day 6 | Day 7 |
|---|---|---|---|---|---|---|---|
| Blank Control Group | 17.4 ± 1.4 | 23.1 ± 1.5 | 24.6 ± 2.0 | 25.9 ± 1.5 | 26.9 ± 0.7 | 27.9 ± 1.5 | 28.7 ± 1.7 |
| Example 1 | 20.1 ± 1.4 | 23.8 ± 1.4 | 24.9 ± 1.0 | 26.3 ± 1.2 | 27.7 ± 1.3 | 29.2 ± 1.4 | 29.4 ± 1.4 |
| Example 8 | 18.0 ± 1.3 | 23.1 ± 0.9 | 24.6 ± 1.0 | 25.6 ± 1.7 | 27.2 ± 2.2 | 28.2 ± 2.2 | 29.2 ± 2.6 |
| Example 3 | 18.0 ± 0.2 | 22.9 ± 0.3 | 24.3 ± 0.9 | 25.2 ± 1.1 | 27.0 ± 1.3 | 28.2 ± 1.9 | 28.5 ± 2.7 |
| Example 4 | 17.6 ± 0.2 | 22.2 ± 0.3 | 23.6 ± 0.6 | 24.7 ± 0.6 | 26.7 ± 0.4 | 27.6 ± 0.8 | 28.2 ± 0.1 |
| Example 22 | 17.1 ± 0.3 | 22.9 ± 0.8 | 23.5 ± 0.9 | 25.2 ± 0.5 | 27.2 ± 1.9 | 27.1 ± 1.8 | 27.4 ± 1.9 |
| Example 18 | 18.2 ± 0.4 | 23.0 ± 0.7 | 24.1 ± 0.4 | 25.6 ± 0.8 | 28.1 ± 1.1 | 29.0 ± 1.4 | 29.0 ± 1.0 |
| Example 24 | 17.7 ± 0.2 | 22.3 ± 0.7 | 24.5 ± 1.0 | 25.2 ± 1.0 | 27.2 ± 1.3 | 28.1 ± 2.0 | 28.9 ± 1.9 |

TABLE 19-continued

Table of Daily Body Weight of Tested Male Mice (g, Mean ± SD)

|  | Day 1 | Day 2 | Day 3 | Day 4 | Day 5 | Day 6 | Day 7 |
|---|---|---|---|---|---|---|---|
| Example 23 | 19.4 ± 0.8 | 24.6 ± 1.2 | 24.5 ± 0.6 | 24.5 ± 0.6 | 25.4 ± 1.2 | 28.1 ± 0.8 | 29.0 ± 0.8 |
| Example 10 | 19.4 ± 0.3 | 24.4 ± 0.6 | 25.5 ± 0.9 | 25.5 ± 0.9 | 26.8 ± 0.9 | 29.2 ± 0.7 | 30.3 ± 0.7 |
| Example 2 | 18.6 ± 0.5 | 24.1 ± 0.4 | 24.7 ± 0.2 | 24.7 ± 0.2 | 26.2 ± 0.6 | 28.8 ± 0.5 | 29.2 ± 0.8 |
| Example 11 | 19.5 ± 0.6 | 23.7 ± 0.8 | 25.4 ± 0.4 | 25.4 ± 0.4 | 27.0 ± 0.5 | 29.0 ± 0.7 | 29.8 ± 1.0 |
| Example 20 | 18.8 ± 1.0 | 24.0 ± 1.1 | 25.3 ± 1.2 | 25.3 ± 1.2 | 26.7 ± 1.2 | 29.0 ± 1.1 | 29.3 ± 0.7 |
| Example 17 | 19.0 ± 0.7 | 24.0 ± 0.7 | 24.6 ± 0.8 | 24.6 ± 0.8 | 26.1 ± 0.7 | 28.1 ± 0.6 | 29.3 ± 1.0 |
| Example 13 | 19.6 ± 0.7 | 23.1 ± 0.6 | 24.4 ± 0.9 | 24.4 ± 0.9 | 26.5 ± 0.5 | 28.3 ± 1.3 | 28.4 ± 0.8 |
| Example 12 | 18.5 ± 0.2 | 24.3 ± 0.6 | 24.9 ± 0.1 | 24.9 ± 0.1 | 26.1 ± 0.7 | 27.8 ± 0.7 | 28.5 ± 0.7 |
| Example 19 | 18.9 ± 1.2 | 20.7 ± 1.1 | 21.3 ± 0.6 | 25.0 ± 2.0 | 24.8 ± 1.9 | 26.5 ± 1.9 | 27.7 ± 2.2 |
| Example 26 | 18.7 ± 0.8 | 23.4 ± 0.5 | 25.0 ± 0.6 | 26.6 ± 1.4 | 27.3 ± 1.3 | 28.3 ± 1.3 | 28.8 ± 1.4 |
| Example 6 | 18.4 ± 0.6 | 21.5 ± 0.9 | 21.6 ± 1.3 | 25.5 ± 0.5 | 25.9 ± 0.9 | 26.9 ± 1.1 | 27.1 ± 1.1 |
| Example 3 | 18.8 ± 0.7 | 23.3 ± 0.1 | 24.3 ± 0.1 | 25.6 ± 0.7 | 26.9 ± 0.8 | 27.9 ± 0.9 | 28.6 ± 0.4 |
| Example 9 | 18.3 ± 0.7 | 23.6 ± 0.7 | 24.1 ± 1.0 | 25.9 ± 1.1 | 27.2 ± 0.5 | 26.9 ± 1.4 | 27.9 ± 1.5 |

TABLE 20

Table of Daily Body Weight of Tested Female Mice (g, Mean ± SD)

|  | Day 1 | Day 2 | Day 3 | Day 4 | Day 5 | Day 6 | Day 7 |
|---|---|---|---|---|---|---|---|
| Blank Control Group | 17.4 ± 1.4 | 22.2 ± 0.3 | 23.4 ± 0.7 | 23.1 ± 0.2 | 24.3 ± 1.6 | 24.7 ± 1.6 | 24.1 ± 1.1 |
| Example 1 | 18.5 ± 0.1 | 22.8 ± 0.3 | 23.2 ± 0.7 | 24.0 ± 0.2 | 25.3 ± 1.6 | 25.7 ± 1.6 | 27.1 ± 1.1 |
| Example 8 | 18.9 ± 0.9 | 22.9 ± 0.9 | 24.3 ± 0.7 | 24.3 ± 1.1 | 25.3 ± 1.4 | 25.8 ± 1.5 | 26.0 ± 2.5 |
| Example 3 | 18.8 ± 0.4 | 22.1 ± 1.2 | 22.7 ± 0.8 | 23.0 ± 1.4 | 23.7 ± 1.9 | 24.1 ± 1.2 | 24.4 ± 1.8 |
| Example 4 | 18.4 ± 0.4 | 21.8 ± 0.5 | 23.2 ± 0.6 | 23.5 ± 1.2 | 24.7 ± 0.9 | 24.2 ± 1.2 | 24.0 ± 0.8 |
| Example 22 | 18.5 ± 0.6 | 21.8 ± 0.3 | 22.9 ± 0.4 | 24.0 ± 1.0 | 25.0 ± 0.4 | 25.3 ± 0.6 | 25.6 ± 0.2 |
| Example 18 | 18.4 ± 0.7 | 22.5 ± 0.8 | 23.8 ± 1.1 | 24.8 ± 1.5 | 24.8 ± 0.6 | 25.4 ± 0.7 | 25.2 ± 1.1 |
| Example 24 | 18.4 ± 0.7 | 22.4 ± 1.0 | 23.4 ± 1.0 | 23.6 ± 0.9 | 24.3 ± 0.6 | 24.7 ± 0.6 | 24.8 ± 1.5 |
| Example 23 | 19.1 ± 0.6 | 22.4 ± 0.4 | 23.0 ± 0.1 | 23.0 ± 0.1 | 24.6 ± 0.4 | 24.8 ± 0.7 | 24.6 ± 0.4 |
| Example 10 | 19.2 ± 0.5 | 21.9 ± 0.4 | 22.4 ± 0.2 | 22.4 ± 0.2 | 22.9 ± 0.6 | 24.1 ± 1.5 | 24.2 ± 1.8 |
| Example 2 | 19.2 ± 0.5 | 22.7 ± 0.6 | 23.2 ± 0.5 | 23.2 ± 0.5 | 24.4 ± 0.2 | 24.6 ± 1.1 | 24.5 ± 1.9 |
| Example 11 | 18.1 ± 0.2 | 21.7 ± 0.2 | 22.4 ± 0.1 | 22.4 ± 0.1 | 23.5 ± 0.4 | 23.2 ± 0.8 | 23.2 ± 0.9 |
| Example 20 | 18.7 ± 0.4 | 21.6 ± 1.0 | 22.1 ± 1.0 | 22.1 ± 1.0 | 23.0 ± 1.4 | 23.3 ± 0.2 | 23.7 ± 0.8 |
| Example 17 | 18.6 ± 1.0 | 21.9 ± 0.4 | 22.7 ± 0.4 | 22.7 ± 0.4 | 23.0 ± 0.4 | 23.1 ± 1.0 | 22.7 ± 1.2 |
| Example 13 | 18.8 ± 1.1 | 21.3 ± 0.3 | 21.8 ± 0.4 | 21.8 ± 0.4 | 23.0 ± 0.5 | 23.2 ± 0.9 | 23.6 ± 0.9 |
| Example 12 | 18.7 ± 0.7 | 21.8 ± 0.6 | 22.6 ± 0.1 | 22.6 ± 0.0 | 23.7 ± 0.6 | 25.3 ± 1.0 | 25.7 ± 1.6 |
| Example 19 | 18.0 ± 0.6 | 20.7 ± 1.1 | 21.3 ± 0.6 | 22.8 ± 0.3 | 23.2 ± 0.7 | 23.3 ± 1.2 | 23.0 ± 1.7 |
| Example 26 | 18.0 ± 0.7 | 21.9 ± 0.3 | 22.1 ± 0.5 | 22.4 ± 0.2 | 22.7 ± 0.3 | 22.6 ± 0.3 | 24.4 ± 0.2 |
| Example 6 | 17.5 ± 0.9 | 21.5 ± 0.9 | 21.6 ± 1.3 | 22.0 ± 1.2 | 22.3 ± 1.9 | 22.4 ± 2.3 | 22.9 ± 2.0 |
| Example 3 | 18.3 ± 0.4 | 21.7 ± 0.2 | 22.3 ± 0.2 | 22.6 ± 0.8 | 23.0 ± 1.4 | 22.6 ± 1.3 | 22.7 ± 0.4 |
| Example 9 | 17.5 ± 0.6 | 22.1 ± 0.9 | 22.1 ± 0.7 | 22.8 ± 0.8 | 22.8 ± 1.0 | 22.7 ± 1.6 | 23.6 ± 1.7 |

The body weight of the animals in each group had a trend of increase with slight fluctuations. Each compound had no side effects on the change of the body weights of the mice at the dosage of 1000 mg/Kg.

All the patents, patent application publications, patent applications and non-patent literatures as cited in the present disclosure are incorporated herein by reference in their entirety.

It is to be understood that the foregoing description relates to exemplary embodiments of the present application and that modifications may be made without departing from the spirit and scope of the present application as set forth in the claims,

What is claimed is:

1. A method for treating ulcerative colitis, comprising administering a therapeutically effective amount of a piperidine-2,6-dione derivative or pharmaceutically acceptable salts thereof to a subject in need thereof, the piperidine-2,6-dione derivative being selected from the group consisting of:

4-acetylamino-2-(1-(2-methoxyethyl)-2,6-dioxopiperidin-3-yl) isoindolin-1,3-dione and pharmaceutically acceptable salts thereof;

4-methylamino-2-(1-(2-methoxyethyl)-2,6-dioxopiperidin-3-yl) isoindolin-1,3-dione and pharmaceutically acceptable salts thereof;

4-dimethylamino-2-(1-(2-methoxyethyl)-2,6-dioxopiperidin-3-yl) isoindolin-1,3-dione and pharmaceutically acceptable salts thereof;

4-fluoro-2-(1-(2-methoxyethyl)-2,6-dioxopiperidin-3-yl) isoindolin-1,3-dione and pharmaceutically acceptable salts thereof;

4,5,6,7-tetrafluoro-2-(1-(2-methoxyethyl)-2,6-dioxopiperidin-3-yl) isoindolin-1,3-dione and pharmaceutically acceptable salts thereof;

4-amino-2-(1-(2-hydroxyethyl)-2,6-dioxopiperidin-3-yl) isoindolin-1,3-dione and pharmaceutically acceptable salts thereof;

5-amino-2-(1-(2-methoxyethyl)-2,6-dioxopiperidin-3-yl) isoindolin-1,3-dione and pharmaceutically acceptable salts thereof;

4-amino-5-hydroxy-2-(1-(2-methoxyethyl)-2,6-dioxopiperidin-3-yl) isoindolin-1,3-dione and pharmaceutically acceptable salts thereof;

4-amino-5-fluoro-2-(1-(2-methoxyethyl)-2,6-dioxopiperidin-3-yl) isoindolin-1,3-dione and pharmaceutically acceptable salts thereof, 4-amino-7-hydroxy-2-(1-(2-methoxyethyl)-2,6-dioxopiperidin-3-yl) isoindolin-1,3-dione and pharmaceutically acceptable salts thereof;

4-acetylamino-2-(1-(3-methoxypropyl)-2,6-dioxopiperidin-3-yl) isoindolin-1,3-dione and pharmaceutically acceptable salts thereof;

4-fluoro-2-(1-(3-methoxypropyl)-2,6-dioxopiperidin-3-yl) isoindolin-1,3-dione and pharmaceutically acceptable salts thereof;

5-amino-2-(1-(3-methoxypropyl)-2,6-dioxopiperidin-3-yl) isoindolin-1,3-dione and pharmaceutically acceptable salts thereof;

4-amino-2-(1-(2-ethoxyethyl)-2,6-dioxopiperidin-3-yl) isoindolin-1,3-dione pharmaceutically acceptable salts thereof; and 4-fluoro-2-(1-(2-ethoxyethyl)-2,6-dioxopiperidin-3-yl) isoindolin-1,3-dione and pharmaceutically acceptable salts thereof;

5-fluoro-2-(1-(2-methoxyethyl)-2,6-dioxopiperidin-3-yl)-isoindolin-1,3-dione and pharmaceutically acceptable salts thereof;

4-amino-2-(1-(4-methoxybutyl)-2,6-dioxopiperidin-3-yl) isoindolin-1,3-dione and pharmaceutically acceptable salts thereof;

4-hydroxy-2-(1-(2-methoxyethyl)-2,6-dioxopiperidin-3-yl) isoindolin-1,3-dione and pharmaceutically acceptable salts thereof;

4-methyl-2-(1-(2-methoxyethyl)-2,6-dioxopiperidin-3-yl)-isoindolin-1,3-dione and pharmaceutically acceptable salts thereof;

4-amino-5-methoxy-2-(1-(2-methoxyethyl)-2,6-dioxopiperidin-3-yl)-isoindolin-1,3-dione and pharmaceutically acceptable salts thereof;

4-amino-2-(1-(3-methoxypropyl)-2,6-dioxopiperidin-3-yl) isoindolin-1,3-dione and pharmaceutically acceptable salts thereof; and 4-amino-2-(1-(2-methoxyethyl)-2,6-dioxopiperidin-3-yl) isoindolin-1,3-dione and pharmaceutically acceptable salts thereof.

2. The method of claim 1, wherein the ulcerative colitis is mild ulcerative colitis, moderate ulcerative colitis, severe ulcerative colitis or ulcerative colitis in remission.

3. The method of claim 1, wherein the subject is human.

4. The method of claim 1, wherein the piperidine-2,6-dione derivative or pharmaceutically acceptable salts thereof is administered orally.

5. The method of claim 4, wherein the piperidine-2,6-dione derivative or pharmaceutically acceptable salts thereof is administered orally in a solid or liquid formulation.

6. The method of claim 5, wherein the solid formulation is a tablet, capsule or sugar-coated pill.

7. The method of claim 6, wherein the tablet is a plain tablet, sugar-coated tablet or film-coated tablet.

8. The method of claim 5, wherein the liquid formulation is a solution or suspension.

9. A method for treating ulcerative colitis, comprising administering a therapeutically effective amount of a piperidine-2,6-dione derivative of formula (II) or pharmaceutically acceptable salts thereof to a subject in need thereof:

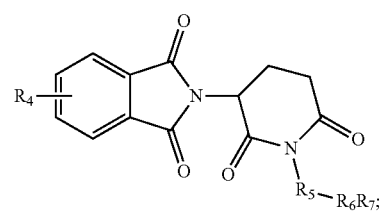

formula (II)

wherein, $R_4$ represents one or more substituents selected from the group consisting of H, halogen, —$C_{1-4}$alkyl, —$NH_2$, —$NHC_{1-4}$alkyl, —$N(C_{1-4}$alkyl$)_2$ and —$NHCOC_{1-4}$alkyl;

$R_5$ represents —$CH_2CH_2$—, —$CH_2CH_2CH_2$— or —$CH_2CH_2CH_2CH_2$—;

$R_6$ represents —S—, —SO—, —$SO_2$—, —NH— or —$N(C_{1-4}$alkyl)-; and $R_7$ represents —H or —$C_{1-4}$alkyl.

10. The method of claim 9, wherein $R_4$ represents one or more substituents selected from the group consisting of —H, —F, —Cl, —Br, —OH, —$CH_3$, —$NHCH_3$, —$NHCH_2CH_3$, —$NH_2$, —$N(CH_3)_2$, —$N(CH_2CH_3)_2$, —$NHCOCH_3$ and —$NHCOCH_2CH_3$;

$R_5$ represents —$CH_2CH_2$—, —$CH_2CH_2CH_2$— or —$CH_2CH_2CH_2CH_2$—;

$R_6$ represents —S—, —SO—, —$SO_2$—, —NH— or —$N(CH_3)$—; and $R_7$ represents —H, —$CH_3$ or —$CH_2CH_3$.

11. The method of claim 9, wherein $R_4$ represents —$NH_2$ or —$NHCOCH_3$;

$R_5$ represents —$CH_2CH_2$—, —$CH_2CH_2CH_2$— or —$CH_2CH_2CH_2CH_2$—;

$R_6$ represents —S—, —SO—, —$SO_2$—, —NH— or —$N(CH_3)$—; and $R_7$ represents —H, —$CH_3$ or —$CH_2CH_3$.

12. The method of claim 9, wherein the piperidine-2,6-dione derivative of formula (II) or pharmaceutically acceptable salts thereof are selected from the group consisting of:

4-amino-2-(1-(2-methylthioethyl)-2,6-dioxopiperidin-3-yl) isoindolin-1,3-dione and pharmaceutically acceptable salts thereof;

4-amino-2-(1-(2-methylsulfinylethyl)-2,6-dioxopiperidin-3-yl) isoindolin-1,3-dione and pharmaceutically acceptable salts thereof; and 4-amino-2-(1-(2-methylsulfonylethyl)-2,6-dioxopiperidin-3-yl) isoindolin-1,3-dione and pharmaceutically acceptable salts thereof.

13. The method of claim 9, wherein the ulcerative colitis is mild ulcerative colitis, moderate ulcerative colitis, severe ulcerative colitis or ulcerative colitis in remission.

14. The method of claim 9, wherein the subject is human.

15. The method of claim 9, wherein the piperidine-2,6-dione derivative or pharmaceutically acceptable salts thereof is administered orally.

16. The method of claim 15, wherein the piperidine-2,6-dione derivative or pharmaceutically acceptable salts thereof is administered orally in a solid or liquid formulation.

17. The method of claim 16, wherein the solid formulation is a tablet, capsule or sugar-coated pill.

18. The method of claim 17, wherein the tablet is a plain tablet, sugar-coated tablet or film-coated tablet.

19. The method of claim 16, wherein the liquid formulation is a solution or suspension.

20. A method for treating ulcerative colitis, comprising administering a therapeutically effective amount of a piperidine-2,6-dione derivative of formula (III) or pharmaceutically acceptable salts thereof to a subject in need thereof:

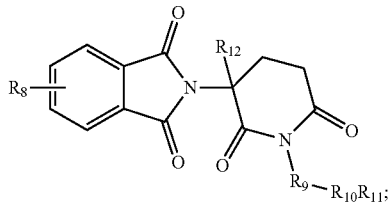

formula (III)

wherein, $R_8$ represents one or more substituents selected from the group consisting of H, halogen, —$C_{1-4}$alkyl, —$NH_2$, —$NHC_{1-4}$alkyl, —$N(C_{1-4}$alkyl$)_2$ and —$NHCOC_{1-4}$alkyl;

$R_9$ represents —$CH_2CH_2$—, —$CH_2CH_2CH_2$— or —$CH_2CH_2CH_2CH_2$—;

$R_{10}$ represents —O—, —S—, —SO—, —$SO_2$—, —NH— or —N($C_{1-4}$alkyl)-;

$R_{11}$ represents —H or —$C_{1-4}$alkyl; and $R_{12}$ represents halogen or —$C_{1-4}$alkyl.

21. The method of claim 20, wherein $R_8$ represents one or more substituents selected from the group consisting of —H, —F, —Cl, —Br, —OH, —$CH_3$, —$NHCH_3$, —$NHCH_2CH_3$, —$NH_2$, —$N(CH_3)_2$, —$N(CH_2CH_3)_2$, —$NHCOCH_3$ and —$NHCOCH_2CH_3$;

$R_9$ represents —$CH_2CH_2$—, —$CH_2CH_2CH_2$— or —$CH_2CH_2CH_2CH_2$—;

$R_{10}$ represents —O—, —S—, —SO—, —SH— or —N($CH_3$)—;

$R_{11}$ represents —H, —$CH_3$ or —$CH_2CH_3$; and $R_{12}$ represents halogen or —$C_{1-4}$alkyl.

22. The method of claim 20, wherein $R_8$ represents —$NH_2$ or —$NHCOCH_3$;

$R_9$ represents —$CH_2CH_2$—, —$CH_2CH_2CH_2$— or —$CH_2CH_2CH_2CH_2$—;

$R_{10}$ represents —O—, —S—, —SO—, —$SO_2$—, —NH— or —N($CH_3$)—;

$R_{11}$ represents —H, —$CH_3$ or —$CH_2CH_3$; and $R_{12}$ represents halogen or —$C_{1-4}$alkyl.

23. The method of claim 20, wherein the piperidine-2,6-dione derivative of formula (III) or pharmaceutically acceptable salts are selected from the group consisting of:

4-amino-2-(1-(2-methoxyethyl)-3-fluoro-2,6-dioxopiperidin-3-yl) isoindolin-1,3-dione and pharmaceutically acceptable salts thereof; and 4-amino-2-(1-(2-methoxyethyl)-3-methyl-2,6-dioxopiperidin-3-yl) isoindolin-1,3-dione and pharmaceutically acceptable salts thereof.

24. The method of claim 20, wherein the ulcerative colitis is mild ulcerative colitis, moderate ulcerative colitis, severe ulcerative colitis or ulcerative colitis in remission.

25. The method of claim 20, wherein the subject is human.

26. The method of claim 20, wherein the piperidine-2,6-dione derivative or pharmaceutically acceptable salts thereof is administered orally.

27. The method of claim 26, wherein the piperidine-2,6-dione derivative or pharmaceutically acceptable salts thereof is administered orally in a solid or liquid formulation.

28. The method of claim 27, wherein the solid formulation is a tablet, capsule or sugar-coated pill.

29. The method of claim 28, wherein the tablet is a plain tablet, sugar-coated tablet or film-coated tablet.

30. The method of claim 27, wherein the liquid formulation is a solution or suspension.

* * * * *